United States Patent
Zur et al.

(10) Patent No.: US 12,233,201 B2
(45) Date of Patent: Feb. 25, 2025

(54) INHALER SYSTEM

(71) Applicant: Norton (Waterford) Limited, Waterford (IE)

(72) Inventors: Amir Zur, Cambridge, MA (US); Xinyu Liu, Winchester, MA (US); Mark Milton-Edwards, Cheshire (GB)

(73) Assignee: Norton (Waterford) Limited, Waterford (IE)

( * ) Notice: Subject to any disclaimer, the term of this patent is extended or adjusted under 35 U.S.C. 154(b) by 0 days.

(21) Appl. No.: 16/906,651

(22) Filed: Jun. 19, 2020

(65) Prior Publication Data
US 2021/0393892 A1    Dec. 23, 2021

(51) Int. Cl.
*A61M 15/00* (2006.01)
*A61B 5/087* (2006.01)
(Continued)

(52) U.S. Cl.
CPC ......... *A61M 15/0001* (2014.02); *A61B 5/087* (2013.01); *A61M 15/0025* (2014.02); *A61M 15/009* (2013.01); *A61M 2016/0024* (2013.01); *A61M 2016/0027* (2013.01); *A61M 16/14* (2013.01); *A61M 2202/064* (2013.01); *A61M 2205/3334* (2013.01); *A61M 2205/3375* (2013.01); *A61M 2205/505* (2013.01);
(Continued)

(58) Field of Classification Search
CPC .......... A61M 15/0001; A61M 15/0025; A61M 2016/0027; A61M 2205/3334; A61M 2202/064; A61M 2205/581; A61M 2205/3375; A61M 2230/40; A61M 2205/505; A61M 15/009; A61M 2016/0024; A61M 2205/52; A61M 16/14; A61B 5/087; G06F 3/0488; G06F 3/167
See application file for complete search history.

(56) References Cited

U.S. PATENT DOCUMENTS 5,694,920 A * 12/1997 Abrams ............ A61M 15/0028
                                               128/200.16
6,216,096 B1 * 4/2001 Obermeier ........... A61B 5/0008
                                                   705/418
(Continued)

FOREIGN PATENT DOCUMENTS

EP    1992381 A1    11/2008
WO    2016043601 A1    3/2016
(Continued)

*Primary Examiner* — Annette Dixon
(74) *Attorney, Agent, or Firm* — Flaster Greenberg P.C.

(57) ABSTRACT

Provided is a system comprising an inhaler. The inhaler comprises a use determination system. The use determination system is configured to determine a parameter relating to airflow during a use of the inhaler by a subject. The use determination system also assigns a time to the use. The system also comprises a user interface, and a processing module. The processing module is configured to determine inhalation information from the parameter, and control the user interface to issue a notification that the inhalation information is available. The notification is issued at a notification time. The processing module is configured to implement a deliberate time delay such that the notification time is delayed relative to the time assigned to the use.

26 Claims, 12 Drawing Sheets

(51) Int. Cl.
  *A61M 16/00* (2006.01)
  *A61M 16/14* (2006.01)
  *G06F 3/0488* (2022.01)
  *G06F 3/16* (2006.01)

(52) U.S. Cl.
  CPC ... *A61M 2205/52* (2013.01); *A61M 2205/581* (2013.01); *A61M 2230/40* (2013.01); *G06F 3/0488* (2013.01); *G06F 3/167* (2013.01)

(56) References Cited

U.S. PATENT DOCUMENTS

| | | | |
|---|---|---|---|
| 6,958,691 | B1 | 10/2005 | Anderson et al. |
| 7,282,029 | B1 | 10/2007 | Poulsen et al. |
| 8,424,517 | B2 | 4/2013 | Sutherland et al. |
| 9,179,260 | B2 | 11/2015 | Ostrander et al. |
| 9,295,793 | B2 | 3/2016 | O'Hara et al. |
| 9,364,619 | B2 | 6/2016 | Polidoro et al. |
| 9,468,729 | B2 | 10/2016 | Sutherland et al. |
| 9,474,871 | B2 | 10/2016 | Feriani et al. |
| 9,483,620 | B2 | 11/2016 | Reimer |
| 9,550,031 | B2 | 1/2017 | Van Sickle et al. |
| 9,555,200 | B2 | 1/2017 | Hosemann et al. |
| 9,555,201 | B2 | 1/2017 | Collins et al. |
| 9,706,946 | B2 | 7/2017 | Brimer et al. |
| 9,734,302 | B2 | 8/2017 | Nielsen et al. |
| 10,016,134 | B2 | 7/2018 | Hansen et al. |
| 10,155,094 | B2 | 12/2018 | Wachtel et al. |
| 10,173,020 | B2 | 1/2019 | Sutherland et al. |
| 10,220,166 | B2 | 3/2019 | Van Sickle et al. |
| 10,255,412 | B2 | 4/2019 | Hogg et al. |
| 10,258,753 | B2 | 4/2019 | Adams et al. |
| 10,272,215 | B2 | 4/2019 | Adams et al. |
| 10,300,227 | B2 | 5/2019 | Sutherland |
| 10,369,305 | B2 | 8/2019 | Li et al. |
| 10,388,412 | B1 | 8/2019 | Koblenski et al. |
| 10,391,270 | B2 | 8/2019 | Adams et al. |
| 10,406,305 | B2 | 9/2019 | Collins et al. |
| 10,556,070 | B2 | 2/2020 | Van Sickle et al. |
| 10,603,450 | B2 | 3/2020 | Sutherland |
| 10,643,742 | B2 | 5/2020 | Hogg et al. |
| 10,668,232 | B2 | 6/2020 | Sutherland et al. |
| 10,688,261 | B2 | 6/2020 | Van Sickle et al. |
| 2005/0026117 | A1* | 2/2005 | Judson .................. G16H 70/40 434/154 |
| 2008/0230057 | A1 | 9/2008 | Sutherland et al. |
| 2010/0250280 | A1 | 9/2010 | Sutherland et al. |
| 2012/0048269 | A1 | 3/2012 | Pardonge et al. |
| 2014/0182584 | A1 | 7/2014 | Sutherland et al. |
| 2016/0144141 | A1 | 5/2016 | Sabharwal et al. |
| 2016/0228657 | A1 | 8/2016 | Sutherland |
| 2016/0314256 | A1 | 10/2016 | Su et al. |
| 2017/0109493 | A1 | 4/2017 | Hogg et al. |
| 2017/0325734 | A1 | 11/2017 | Sutherland et al. |
| 2018/0011988 | A1 | 1/2018 | Ziegler et al. |
| 2018/0085540 | A1 | 3/2018 | Dantsker et al. |
| 2018/0140786 | A1* | 5/2018 | Calderon Oliveras ...................... A61M 15/0071 |
| 2018/0161530 | A1 | 6/2018 | Ganton et al. |
| 2018/0200460 | A1 | 7/2018 | Ziegler et al. |
| 2018/0236187 | A1 | 8/2018 | Jung et al. |
| 2019/0001085 | A1 | 1/2019 | Cottenden et al. |
| 2019/0015608 | A1 | 1/2019 | Glusker et al. |
| 2019/0030262 | A1 | 1/2019 | Ziegler et al. |
| 2019/0060590 | A1 | 2/2019 | Starr et al. |
| 2019/0102522 | A1 | 4/2019 | Barrett et al. |
| 2019/0105450 | A1 | 4/2019 | Sutherland et al. |
| 2019/0111220 | A1 | 4/2019 | Richardson et al. |
| 2019/0151577 | A1 | 5/2019 | Jung et al. |
| 2019/0175847 | A1 | 6/2019 | Pocreva et al. |
| 2019/0175850 | A1 | 6/2019 | Petit |
| 2019/0189258 | A1 | 6/2019 | Barrett et al. |
| 2019/0272925 | A1 | 9/2019 | Barrett et al. |
| 2019/0298942 | A1 | 10/2019 | Koblenski et al. |
| 2019/0307648 | A1 | 10/2019 | Bartos |
| 2019/0313949 | A1 | 10/2019 | Orsatti et al. |
| 2020/0001026 | A1 | 1/2020 | Starr et al. |
| 2020/0058403 | A1 | 2/2020 | Barrett et al. |
| 2020/0086069 | A1 | 3/2020 | Riebe et al. |
| 2020/0155773 | A1 | 5/2020 | Zipkes et al. |
| 2020/0376209 | A1 | 12/2020 | Mohammed et al. |
| 2020/0384216 | A1 | 12/2020 | Eicher et al. |

FOREIGN PATENT DOCUMENTS

| | | | |
|---|---|---|---|
| WO | WO-2017141194 A1 * | 8/2017 | ............ G16H 20/10 |
| WO | 2018091678 A1 | 5/2018 | |
| WO | 2018160073 A1 | 9/2018 | |
| WO | 2019022620 A1 | 1/2019 | |
| WO | 2019209994 A1 | 10/2019 | |
| WO | 2019226576 A1 | 11/2019 | |
| WO | 2020127139 A1 | 6/2020 | |
| WO | 2020182655 A1 | 9/2020 | |
| WO | 2020225662 A1 | 11/2020 | |

* cited by examiner

//INHALER SYSTEM

TECHNICAL FIELD

This disclosure relates to an inhaler system, and particularly systems and methods for notifying the subject with information relating to their inhaler use.

BACKGROUND

Many respiratory diseases, such as asthma or chronic obstructive pulmonary disease (COPD), are life-long conditions where treatment involves the long-term administration of medicaments to manage the patients' symptoms and to decrease the risks of irreversible changes. There is currently no cure for diseases like asthma and COPD. Treatment takes two forms. First, a maintenance aspect of the treatment is intended to reduce airway inflammation and, consequently, control symptoms in the future. The maintenance therapy is typically provided by inhaled corticosteroids, alone or in combination with long-acting bronchodilators and/or muscarinic antagonists. Secondly, there is also a rescue (or reliever) aspect of the therapy, where patients are given rapid-acting bronchodilators to relieve acute episodes of wheezing, coughing, chest tightness and shortness of breath.

Inhalers equipped with use monitoring electronics are known. Such inhalers may, for example, provide the subject with information relevant to the patient's/subject's technique when using the inhaler.

SUMMARY

The present disclosure provides a system for providing inhalation information to a subject. An example of such a system includes an inhaler comprising a use determination system. The use determination system is configured to determine a parameter relating to airflow during a use of the inhaler by a subject. The use determination system also assigns a time to the use.

The exemplary system comprises a user interface, and a processing module. The processing module is configured to determine inhalation information from the parameter, and control the user interface to issue a notification that the inhalation information is available. The notification is issued at a notification time. The processing module is configured to implement a deliberate time delay such that the notification time is delayed relative to the time assigned to the use.

The subject may respond to a notification that the inhalation information is available by immediately accessing this inhalation information, e.g. by inputting one or more commands which causes or cause the user interface to communicate the inhalation information. There is a risk that the user reacts to the inhalation information by immediately inhaling a further dose of the medicament in instances, for example, where the inhalation information indicates that the user's first inhalation was performed incorrectly or was not an optimal inhalation. Such a further dose may not be necessary, and such behavior may increase the risk of the user taking too much of the medication.

By deliberately delaying the notification that the inhalation information is available relative to the time at which the use of the inhaler took place, the risk that the subject reactively takes too much of the medicament may be lessened. The safety of the system may be correspondingly improved.

BRIEF DESCRIPTION OF THE DRAWINGS

The embodiments will now be described in more detail with reference to the accompanying drawings, which are not intended to be limiting.

DETAILED DESCRIPTION

Figure 1:
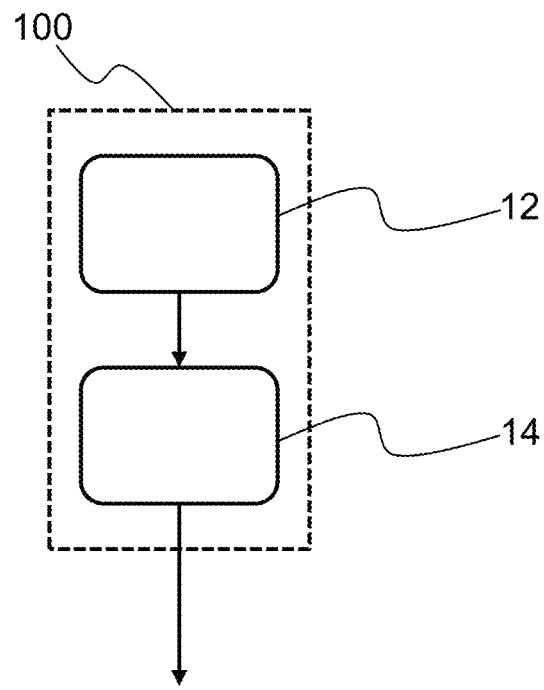
FIG. 1 shows a block diagram of an inhaler according to an example.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the figures to indicate the same or similar parts.

Asthma and COPD are chronic inflammatory disease of the airways. They are both characterized by variable and recurring symptoms of airflow obstruction and bronchospasm. The symptoms include episodes of wheezing, coughing, chest tightness and shortness of breath.

The symptoms are managed by avoiding triggers and by the use of medicaments, particularly inhaled medicaments. The medicaments include inhaled corticosteroids (ICSs) and bronchodilators.

Inhaled corticosteroids (ICSs) are steroid hormones used in the long-term control of respiratory disorders. They function by reducing the airway inflammation. Examples include budesonide, beclomethasone (dipropionate), fluticasone (propionate or furoate), mometasone (furoate), ciclesonide and dexamethasone (sodium). Parentheses indicate preferred salt or ester forms. Particular mention should be made of budesonide, beclomethasone and fluticasone, especially budesonide, beclomethasone dipropionate, fluticasone propionate and fluticasone furoate.

Different classes of bronchodilators target different receptors in the airways. Two commonly used classes are $\beta_2$-agonists and anticholinergics.

$\beta_2$-Adrenergic agonists (or "$\beta_2$-agonists") act upon the $\beta_2$-adrenoceptors which induces smooth muscle relaxation, resulting in dilation of the bronchial passages. They tend to be categorised by duration of action. Examples of long-acting $\beta_2$-agonists (LABAs) include formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride) and vilanterol (triphenylacetate). Examples of short-acting $\beta_2$-agonists (SABA) are albuterol (sulfate) and terbutaline (sulfate). Particular mention should be made of formoterol, salmeterol, indacaterol and vilanterol, especially formoterol fumarate, salmeterol xinafoate, indacaterol maleate and vilanterol triphenylacetate.

Typically short-acting bronchodilators provide a rapid relief from acute bronchoconstriction (and are often called "rescue" or "reliever" medicines), whereas long-acting bronchodilators help control and prevent longer-term symptoms. However, some rapid-onset long-acting bronchodilators may be used as rescue medicines, such as formoterol (fumarate). Thus, a rescue medicine provides relief from acute bronchoconstriction. The rescue medicine is taken as-needed/prn (pro re nata). The rescue medicine may also be in the form of a combination product, e.g. ICS-formoterol (fumarate), typically budesonide-formoterol (fumarate) or beclomethasone (dipropionate)-formoterol (fumarate). Thus, the rescue medicine is preferably a SABA or a rapid-acting LABA, more preferably albuterol (sulfate) or formoterol (fumarate), and most preferably albuterol (sulfate).

Anticholinergics (or "antimuscarinics") block the neurotransmitter acetylcholine by selectively blocking its receptor in nerve cells. On topical application, anticholinergics act predominantly on the $M_3$ muscarinic receptors located in the airways to produce smooth muscle relaxation, thus producing a bronchodilatory effect. Examples of long-acting muscarinic antagonists (LAMAs) include tiotropium (bromide), oxitropium (bromide), aclidinium (bromide), umeclidinium (bromide), ipratropium (bromide) glycopyrronium (bromide), oxybutynin (hydrochloride or hydrobromide), tolterodine (tartrate), trospium (chloride), solifenacin (succinate), fesoterodine (fumarate) and darifenacin (hydrobromide). Particular mention should be made of tiotropium, aclidinium, umeclidinium and glycopyrronium, especially tiotropium bromide, aclidinium bromide, umeclidinium bromide and glycopyrronium bromide.

A number of approaches have been taken in preparing and formulating these medicaments for delivery by inhalation, such as via a dry powder inhaler (DPI), a pressurized metered dose inhaler (pMDI) or a nebulizer.

According to the GINA (Global Initiative for Asthma) Guidelines, a step-wise approach is taken to the treatment of asthma. At step 1, which represents a mild form of asthma, the patient is given an as needed SABA, such as albuterol sulfate. The patient may also be given an as-needed low-dose ICS-formoterol, or a low-dose ICS whenever the SABA is taken. At step 2, a regular low-dose ICS is given alongside the SABA, or an as-needed low-dose ICS-formoterol. At step 3, a LABA is added. At step 4, the doses are increased and at step 5, further add-on treatments are included such as an anticholinergic or a low-dose oral corticosteroid. Thus, the respective steps may be regarded as treatment regimens, which regimens are each configured according to the degree of acute severity of the respiratory disease.

COPD is a leading cause of death worldwide. It is a heterogeneous long-term disease comprising chronic bronchitis, emphysema and also involving the small airways. The pathological changes occurring in patients with COPD are predominantly localised to the airways, lung parenchyma and pulmonary vasculature. Phenotypically, these changes reduce the healthy ability of the lungs to absorb and expel gases.

Bronchitis is characterised by long-term inflammation of the bronchi. Common symptoms may include wheezing, shortness of breath, cough and expectoration of sputum, all of which are highly uncomfortable and detrimental to the patient's quality of life. Emphysema is also related to long-term bronchial inflammation, wherein the inflammatory response results in a breakdown of lung tissue and progressive narrowing of the airways. In time, the lung tissue loses its natural elasticity and becomes enlarged. As such, the efficacy with which gases are exchanged is reduced and respired air is often trapped within the lung. This results in localised hypoxia, and reduces the volume of oxygen being delivered into the patient's bloodstream, per inhalation. Patients therefore experience shortness of breath and instances of breathing difficulty.

Patients living with COPD experience a variety, if not all, of these symptoms on a daily basis. Their severity will be determined by a range of factors but most commonly will be correlated to the progression of the disease. These symptoms, independent of their severity, are indicative of stable COPD and this disease state is maintained and managed through the administration of a variety drugs. The treatments are variable, but often include inhaled bronchodilators, anticholinergic agents, long-acting and short-acting $\beta_2$-agonists and corticosteroids. The medicaments are often administered as a single therapy or as combination treatments.

Patients are categorised by the severity of their COPD using categories defined in the GOLD Guidelines (Global Initiative for Chronic Obstructive Lung Disease, Inc.). The categories are labelled A-D and the recommended first choice of treatment varies by category. Patient group A are recommended a short-acting muscarinic antagonist (SAMA) prn or a short-acting $\beta_2$-aginist (SABA) prn. Patient group B are recommended a long-acting muscarinic antagonist (LAMA) or a long-acting $\beta_2$-aginist (LABA). Patient group C are recommended an inhaled corticosteroid (ICS)+a LABA, or a LAMA. Patient group D are recommended an ICS+a LABA and/or a LAMA.

Patients suffering from respiratory diseases like asthma or COPD suffer from periodic exacerbations beyond the baseline day-to-day variations in their condition. An exacerbation is an acute worsening of respiratory symptoms that require additional therapy, i.e. a therapy going beyond their maintenance therapy.

For asthma, the additional therapy for a moderate exacerbation are repeated doses of SABA, oral corticosteroids and/or controlled flow oxygen (the latter of which requires hospitalization). A severe exacerbation adds an anticholinergic (typically ipratropium bromide), nebulized SABA or IV magnesium sulfate.

For COPD, the additional therapy for a moderate exacerbation are repeated doses of SABA, oral corticosteroids and/or antibiotics. A severe exacerbation adds controlled flow oxygen and/or respiratory support (both of which require hospitalization). An exacerbation within the meaning of the present disclosure includes both moderate and severe exacerbations.

Provided is a system comprising an inhaler. The inhaler comprises a use determination system. The use determination system is configured to determine a parameter relating to airflow during a use of the inhaler by a subject. The use determination system also assigns a time to the use. The system also comprises a user interface and/or a processing module. The processing module is configured to determine inhalation information from the parameter. The processing module is also configured to control the user interface to issue a notification that the inhalation information is available. The notification is issued at a notification time. The processing module is configured to implement a deliberate time delay such that the notification time is delayed relative to the time assigned to the use.

The term "deliberate time delay" refers to an intentional time delay which is implemented by the processing module, and is thus distinct from intrinsic or unintentional time delays. The term "deliberate time delay" is intended to mean an extrinsic time delay which is determined by the processing module, e.g. using a clock module included in the processing module, with reference to the time assigned to the use of the inhaler.

Intrinsic or unintentional time delays may be associated with, for instance, the time taken for transmitting of the parameter from the use determination system, receiving the parameter by the processing module, the processing module transmitting control signals for controlling the user interface, the user interface receiving the control signals, and the user interface issuing the notification in response to the control signals.

The deliberate time delay may, for example, be implemented such as to intentionally delay the transmission of the control signals for controlling the user interface to issue the notification.

By the deliberate time delay being determined with reference to the time assigned to the use of the inhaler, certain intrinsic or unintentional time delays may be accounted for in the determination of the notification time.

In a non-limiting example, if the processing module determines that the time delay which would otherwise be deliberately implemented has already been realized due to an intrinsic or unintentional time delay, the processing module may control the user interface to issue the notification with no intentional time interval being implemented from making this determination to controlling the user interface to issue the notification.

The inhaler may be configured to deliver a medicament to a subject. The inhaler may, for example, comprise a medicament reservoir containing the medicament.

Whilst not essential in the context of the present disclosure, the system may comprise at least one further inhaler. The at least one further inhaler may be configured to deliver one or more further medicaments to the subject. This would be the same subject to whom the medicament is administered via the inhaler. One or more (or each) of the at least one further inhaler may, for example, comprise a respective further medicament reservoir containing the further medicament.

The medicament and the further medicament may be the same as or different from each other, but usually they will be different from each other.

In a non-limiting example, the medicament is a rescue medicament for use by the subject as needed, and the further medicament is a maintenance medicament which is used by the subject according to a predetermined treatment regimen.

The rescue medicament is as defined hereinabove and is typically a SABA or a rapid-onset LABA, such as formoterol (fumarate). The rescue medicament may also be in the form of a combination product, e.g. ICS-formoterol (fumarate), typically budesonide-formoterol (fumarate) or beclomethasone (dipropionate)-formoterol (fumarate). Such an approach is termed "MART" (maintenance and rescue therapy).

In a non-limiting example, the medicament is selected from albuterol (sulfate), budesonide, beclomethasone (dipropionate), fluticasone (propionate or furoate), formoterol (fumarate), salmeterol (xinafoate), indacaterol (maleate), vilanterol (triphenylacetate), tiotropium (bromide), aclidinium (bromide), umeclidinium (bromide), glycopyrronium (bromide), salmeterol (xinafoate) combined with fluticasone (propionate or furoate), beclomethasone (dipropionate) combined with albuterol (sulfate), and budesonide combined with formoterol (fumarate).

More generally, the medicament, the further medicament, and any other medicaments included in inhalers of the system, may comprise any suitable active pharmaceutical ingredient. Thus, any class of medication may be delivered by, in other words housed within, the inhalers included in the system. The system permits consolidated handling and communicating of usage information, e.g. inhalation information, irrespective of the particular medications which are delivered by the inhaler(s).

The inhaler comprises a use determination system. The use determination system is configured to determine a parameter relating to airflow during a use of the inhaler by the subject.

The system (e.g., the use determination system) also comprises a processing module which determines inhalation information from the parameter. The processing module may include a general purpose processor, a special purpose processor, a DSP, a microcontroller, an integrated circuit, and/or the like that may be configured using hardware and/or software to perform the functions described herein for the processing module. The processing module may be included partially or entirely on the inhaler, a user device, and/or a server.

The processing module may include a power supply, memory, and/or a battery.

In an embodiment, the use determination system comprises a sensor for detecting the parameter. Such a sensor may, for example, comprise a pressure sensor, such as an absolute or differential pressure senor.

In a non-limiting example, the use determination system comprises a mechanical switch configured to be actuated prior to, during, or after use of the inhaler. In certain examples, the use determination system employs the sensor in combination with the mechanical switch in order to determine the parameter relating to airflow during a use of the inhaler by the subject.

The inhaler may, for instance, comprise a mouthpiece through which the user performs the inhalation, and a mouthpiece cover. In such an example, the mechanical switch may be configured to be actuated when the mouthpiece cover is moved to expose the mouthpiece.

In an embodiment, if the switch is actuated but no airflow is detected by the sensor, the parameter may be indicative of a use of the inhaler in which no inhalation has taken place. The inhalation information indicated as being available by the corresponding notification may thus indicate a "no inhalation event."

Such a "no inhalation event" may, for example, be determined on the basis of a predetermined time elapsing during which no inhalation is sensed by the sensor following actuation of the mechanical switch, e.g. by opening of the mouthpiece cover.

If the switch is actuated but the sensor detects a value relating to the airflow which is equal to or lower than a first predetermined threshold, the parameter may be indicative of a low inhalation event having taken place. The inhalation information indicated as being available by the corresponding notification may thus indicate a "low inhalation event".

If the switch is actuated but the sensor detects a value relating to the airflow which exceeds a second predetermined threshold, the parameter may be indicative of an excessive inhalation event having taken place. The inhalation information indicated as being available by the corresponding notification may thus indicate an "excessive inhalation event".

In a non-limiting example, the inhaler comprises an air vent through which air is drawn into the inhaler, and an airflow channel which guides the air towards the mouthpiece during an inhalation performed by the subject using the inhaler. The above-described "excessive inhalation event" may, for example, be alternatively or additionally communicated to the user via the user interface as an error message indicating that an air vent of the inhaler is blocked or obstructed during the use of the inhaler.

If the switch is actuated but the sensor detects a value relating to the airflow which exceeds the abovementioned first predetermined threshold, is lower than the abovementioned second predetermined threshold, and is equal to or lower than a third predetermined threshold which is between the first and second predetermined thresholds, the parameter may be indicative of a fair inhalation event having taken place. The inhalation information indicated as being available by the corresponding notification may thus indicate a "fair inhalation event".

If the switch is actuated and the sensor detects a value relating to the airflow which is equal to or lower than the abovementioned second predetermined threshold, and greater than the third predetermined threshold, the parameter may be indicative of a good inhalation event having taken place. The inhalation information indicated as being available by the corresponding notification may thus indicate a "good inhalation event".

The value may be proportional to the sensed airflow such that a higher value is determined for higher airflows. The value relating to airflow may be, for instance, the peak inhalation flow (PIF) during the inhalation. In such an example, the first predetermined threshold may be 30 liters per minute, the second predetermined threshold may be 200 liters per minutes, and the third predetermined threshold may be 45 liters per minute.

The processing module may, for example, control the user interface to communicate, e.g. display, the "no inhalation event", "low inhalation event", "fair inhalation event", "good inhalation event", "excessive inhalation event"/"possible air vent block" message, and/or a value relating to the peak inhalation flow.

The actual value of the peak inhalation flow may, for instance, be communicated via the user interface. Alternatively or additionally, the peak inhalation flow may be communicated as being higher or lower than one or more of the above-described predetermined thresholds, e.g. less than or equal to 30 liters per minute in the case of a low or no inhalation event, more than 30 liters per minute in the case of a fair inhalation event (but less than or equal to 45 liters per minute), more than 45 liters per minute (but less than or equal to 200 liters per minute) in the case of a normal inhalation event, more than 200 liters per minute in the case of an excessive inhalation event/possible air vent block, etc.

Alternatively or additionally, the inhalation information may indicate an inhalation duration, such as a "short inhalation event" or a "good inhalation event". As one example, an inhalation duration may be considered a "short inhalation event" when the parameter relating to airflow indicates an inhalation that lasted less than a threshold, such as 4-6 seconds. Conversely, if the parameter indicates an inhalation that lasted longer than the threshold, then the inhalation information may indicate a "good inhalation event." In such examples, the inhalation information indicated as being available by the corresponding notification may thus indicate a "short inhalation event" or a "good inhalation event."

As briefly described above, the notification is issued at a notification time, and the notification time is deliberately delayed relative to the time assigned to the use.

More generally, the use determination system is further configured to assign a time to the use of the inhaler by the subject. The time assigned to the use of the inhaler by the subject may be regarded as "an assignment time".

The use determination system may implement this time assignment, e.g. time-and-date stamping, of the determined use in any suitable manner.

For example, the use determination system may comprise a clock module for assigning the time, e.g. time-and-date stamp, to the determined use. The clock module may be implemented via a processor or other type of integrated circuit. The clock module may be part of the processing module. The clock module may include distinct memory or may share memory with the processing module. The processing module of the system may, in certain examples, be configured to synchronize the clock module of the inhaler with a further clock module included in the processing module.

Determination that a use of the inhaler has taken place, e.g. due to actuation of the above-described mechanical switch, may trigger the use determination system to assign the time, e.g. the time and date, provided by the clock module coinciding with the determined use.

It is noted that when the system comprises more than one inhaler, one or more (or each) of the respective clock modules included in the use determination systems of each of the inhalers may, for instance, be synchronized to the further clock module included in the processing module.

The further clock module may, for instance, receive the time of the time zone in which the processing module is situated. The processing module may, for example, transmit the time of the time zone to the respective clock modules, thereby to permit the clock modules to be synchronized according to the time in which the subject and their inhaler(s) is or are located. Time stamping of the respective parameter/inhaler usage data may thus correspond to the time of day or night at the subject's geographical location. This is particularly advantageous given the relevance of, for example, night time rescue medicament use to the risk of an impending respiratory disease exacerbation.

The system may thus, for example, monitor the day time and night time rescue inhaler usage of a subject who has travelled across time zones. Alternatively or additionally, reminders issued by the system, e.g. via the user interface, to remind the subject to administer a maintenance medicament may account for the time of day or night at the subject's location.

Further, it should be appreciated that in some examples, the clock module may operate as an internal counter. When operating as an internal counter, the clock module may provide a relative count (e.g., as opposed to providing a mean solar time, such as a local mean time) that may be started when, for example, the use determination system is woken out of an energy-saving sleep mode for a first time (e.g., after the mouthpiece cover is opened for the first time).

The system comprises a user interface, and the processing module controls the user interface to issue, for example display, a notification that the inhalation information determined from the above-described parameter relating to airflow during the use of the inhaler by the subject is available.

The user interface may, for instance, be further configured to enable the inhalation information to be communicated, e.g. displayed. The processing module may be configured to control the user interface to communicate, e.g. display, the inhalation information in response to a user input made via the user interface.

In an embodiment, the user interface is at least partly defined by a first user interface of a user device. The user device may, for example, be at least one selected from a personal computer, a tablet computer, and a smart phone.

In a non-limiting example, the processing module is at least partly included in a first processing module included in the user device. In other non-limiting examples, the processing module is not included in a user device. The processing module (or at least part of the processing module) may, for example, be provided in a server, e.g. a remote server. For example, the processing module may be implemented on any combination of the inhaler, the user device, and/or a remote server. As such, any combination of the functions or processing described with reference to the processing module may be performed by a processing module residing on the inhaler, the user device, and/or a server. For instance, the use determination system residing on the inhaler may capture usage information at the inhaler (e.g., such as a use or manipulation of the inhaler by the user (such as the opening of a mouthpiece cover and/or the actuation of a switch) and/or the parameter relating to airflow during a user of the inhaler), while the processing module residing on any combination of the inhaler, the user device, and/or server may determine inhalation parameters based on the parameter relating to airflow during a user of the inhaler and/or determine notifications associated with the inhalation parameters.

The processing module is configured to issue the notification at a notification time. For example, the processing module is configured to control the user interface to issue the notification at the notification time. As briefly described above, the notification time is deliberately delayed relative to the time assigned to the use.

The subject/patient/user may respond to a notification that the inhalation information relating to a use of the inhaler is available by immediately accessing this information. In the scenario that the inhalation information is indicative of an incomplete inhalation of the medicament delivered by the inhaler, there is a risk that the user reacts by immediately inhaling a further dose of the medicament. Such a further dose may not be necessary, and such behavior may increase the risk of the user taking too much of the medication. By deliberately delaying the notification that the inhalation information is available relative to the time at which the use of the inhaler took place, the risk that the subject reactively takes too much of the medicament may be lessened. This means that the safety of the system can be improved relative to a system in which no such deliberate time delay is implemented.

For example, the notification time may be at least 5 minutes after the time assigned to the use (e.g., the deliberate time delay may be at least 5 minutes). This minimum delay may assist to avoid that the subject is triggered by the inhalation information contained in the notification to re-use the inhaler again too soon after the use to which the notification relates.

Alternatively or additionally, the notification time may be less than 48 hours after the time assigned to the use. In this manner, the notification is issued within a timeframe in which the subject may recollect the use to which the inhalation information relates. This may assist the subject to use the notified inhalation information as feedback in order to correct any faulty technique in their use of the inhaler.

When, on the other hand, the inhalation information is indicative of correct use of the inhaler, by notifying the user/subject with the inhalation information within such a timeframe, the subject's correct use of the inhaler may be correspondingly encouraged or reinforced.

In a non-limiting example, the use determination system is configured such that a time (e.g., a time-and-date stamp) is assigned to the use of the inhaler, e.g. each use of the inhaler, and the notification time is a predetermined time on a day which is subsequent to the day indicated by the time assigned to the use. The user/subject may, for example, be notified on the day after the day on which the use of the inhaler has taken place.

For example, if a use of the inhaler is determined by the use determination system between 00:00:00 and 23:59:59 on a given day, the processing module will issue the notification at a predetermined time between 00:00:00 and 23:59:59 on the immediately following day.

The notification may, for example, be issued at 01:00:00, 02:00:00, 03:00:00, 04:00:00, 05:00:00, 06:00:00, 07:00:00, 08:00:00, 09:00:00, 10:00:00, 11:00:00, 12:00:00, 13:00:00, 14:00:00, 15:00:00, 16:00:00, 17:00:00, 18:00:00, 19:00:00, 20:00:00, 21:00:00, 22:00:00, 23:00:00 on the day immediately after the day on which the time is assigned to the use of the inhaler.

This may, for example, be additionally subject to the above-described condition that the notification is issued at least 5 minutes after the time assigned to the use.

The system may, for example, be configurable such that the user can select the predetermined time on the day subsequent to the day included in the time-and-date stamp that they are notified that the inhalation information is available.

The above-described synchronization between the clock module of the use determination system and the further clock module of the processing module may assist in terms of enabling the notification time to be on a day which is subsequent to the day included in the time-and-date stamp.

Further provided is a method comprising: receiving a parameter relating to airflow during a use of an inhaler by a subject; receiving a time assigned to the use, e.g. each use, of the inhaler; determining inhalation information from the parameter; and controlling a user interface to issue a notification comprising the inhalation information at a notification time. The controlling comprises implementing a deliberate time delay which delays the notification time relative to the time assigned to the use.

A computer program is also provided, which computer program comprises computer program code which is adapted, when the computer program is run on a computer, to implement the method. In an example, the computer code may reside partially or entirely on a user device (e.g., as a mobile application residing on the user device).

The embodiments described herein for the system are applicable to the method and the computer program. Moreover, the embodiments described for the method and computer program are applicable to the system.

FIG. 1 shows a block diagram of an inhaler 100 according to a non-limiting example. The inhaler 100 comprises a use determination system 12 which determines the parameter relating to airflow during a use of the inhaler by a subject. The parameter is received by a transmission module 14, as represented in FIG. 1 by the arrow between the block representing the use determination system 12 and the block representing the transmission module 14. The transmission module 14 encrypts data based on the parameter, and transmits the encrypted data, as represented in FIG. 1 by the arrow pointing away from the transmission module 14 block. The transmission of the encrypted data by the transmission module 14 may, for example, be wireless.

The use determination system 12 may include one or more components used to determine the parameter. For example, the use determination system 12 may, for instance, comprise a mechanical switch configured to be actuated prior to, during, or after use of the respective inhaler, as previously described.

In a non-limiting example, the inhaler 100 comprises a medicament reservoir (not visible in FIG. 1), and a dose metering assembly (not visible in FIG. 1) configured to meter a dose of the rescue medicament from the reservoir. The use determination system 12 may be configured to register the metering of the dose by the dose metering assembly, each metering being thereby indicative of a use (or attempted use) of the inhaler 100. One non-limiting example of the dose metering assembly will be explained in greater detail with reference to FIGS. 12-16.

Alternatively or additionally, the use determination system 12 may register each inhalation in different manners and/or based on additional or alternative feedback. For example, the use determination system 12 is configured to register a use or attempted use of the inhaler by the subject when the feedback from a suitable sensor (not visible in FIG. 1) indicates that an inhalation by the subject has occurred, for example when a pressure change measurement or flow rate exceeds a predefined threshold associated with an inhalation, and/or when a duration of a pressure change is above a threshold exceeds a predefined threshold associated with a low duration inhalation or a good duration inhalation.

A sensor, such as a pressure sensor, may, for example, be included in the use determination system 12 in order to determine the parameter relating to airflow during use, e.g. each use, of the inhaler. When a pressure sensor is included in the use determination system 12, the pressure sensor may, for instance, be used to confirm that, or assess the degree to which, a dose metered via the dose metering assembly is inhaled by the subject, as will be described in greater detail with reference to FIGS. 2 and 12-16.

More generally, the use determination system 12 may comprise a sensor for detecting a parameter relating to airflow during inhalation of the respective medicament performed by the subject. In other words, the usage parameter comprises a parameter relating to airflow during inhalation of the medicament.

The parameter may comprise, for example, at least one of a peak inhalation flow, an inhalation volume, a time to peak inhalation flow, and an inhalation duration. In such examples, the parameter may comprise a numerical value for the peak inhalation flow, the inhalation volume, the time to peak inhalation flow, and/or the inhalation duration.

A pressure sensor may be particularly suitable for measuring the parameter, since the airflow during inhalation by the subject may be monitored by measuring the associated pressure changes. As will be explained in greater detail with reference to FIGS. 12-16, the pressure sensor may be located within or placed in fluid communication with a flow pathway through which air and the medicament is drawn by the subject during inhalation. Alternative ways of measuring the parameter, such as via a suitable flow sensor, can also be used.

An inhalation may be associated with a decrease in the pressure in the airflow channel of the inhaler relative to when no inhalation is taking place. The point at which the pressure change is at its greatest may correspond to the peak inhalation flow. The pressure sensor may detect this point in the inhalation.

The pressure change associated with an inhalation may alternatively or additionally be used to determine an inhalation volume. This may be achieved by, for example, using the pressure change during the inhalation measured by the pressure sensor to first determine the flow rate over the time of the inhalation, from which the total inhaled volume may be derived.

The pressure change associated with an inhalation may alternatively or additionally be used to determine an inhalation duration. The time may be recorded, for example, from the first decrease in pressure measured by the pressure sensor, coinciding with the start of the inhalation, to the pressure returning to a pressure corresponding to no inhalation taking place.

The inhalation parameter may alternatively or additionally include the time to peak inhalation flow. This time to peak inhalation flow parameter may be recorded, for example, from the first decrease in pressure measured by the pressure sensor, coinciding with the start of the inhalation, to the pressure reaching a minimum value corresponding to peak flow.

Figure 2:
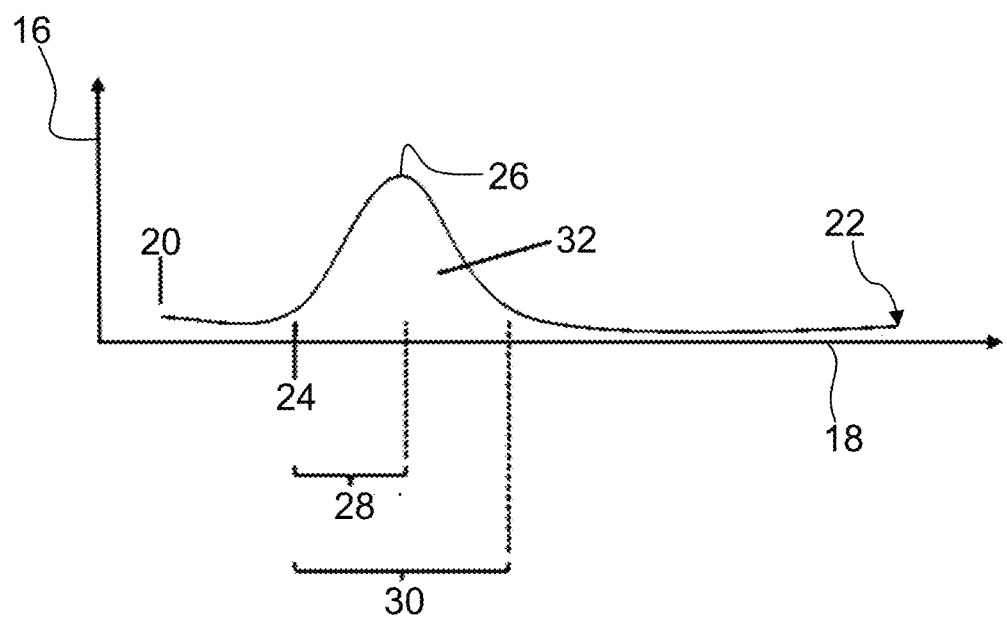
FIG. 2 shows a graph of flow rate versus time during use of an inhaler according to an example.

FIG. 2 shows a graph of flow rate 16 versus time 18 during use of an inhaler 100 according to a non-limiting example. The use determination system 12 in this example comprises a mechanically operated switch in the form of a switch which is actuated when a mouthpiece cover of the inhaler 100 is opened. The mouthpiece cover is opened at point 20 on the graph. In this example, the use determination system 12 further comprises a pressure sensor.

When the mouthpiece cover is opened, the use determination system 12 is woken out of an energy-saving sleep mode, and a new inhalation event is registered. The inhalation event is also assigned an open time corresponding to how much time, for example milliseconds, elapses since the inhaler 100 wakes from the sleep mode. Point 22 corresponds to the cap closing or 60 seconds having elapsed since point 20. At point 22, detection ceases.

Once the mouthpiece cover is open, the use determination system 12 looks for a change in the air pressure, as detected using the pressure sensor. The start of the air pressure change is registered as the inhale event time 24. The point at which the air pressure change is greatest corresponds to the peak inhalation flow 26. The use determination system 12 records the peak inhalation flow 26 as a flow of air, measured in units of 100 mL per minute, which flow of air is transformed from the air pressure change. Thus, in this example, the parameter comprises a value of the peak inhalation flow in units of 100 mL per minute.

The time to peak inhalation flow 28 corresponds to the time taken in milliseconds for the peak inhalation flow 26 to be reached. The inhalation duration 30 corresponds to the duration of the entire inhalation in milliseconds. The area under the graph 32 corresponds to the inhalation volume in milliliters.

The inhalation information provided via the user interface may, additionally or alternatively to providing the inhalation parameter(s) as numerical values, provide a classification of one or more (or each) inhalation event(s). For example, if the peak inhalation flow is between 0 and 30 liters per minute, the inhalation event is classified as "low inhalation" (less than or equal to 30 liters per minute) or as "no inhalation", if no inhalation is detected within 60 seconds of the mouthpiece cover being open. If the peak inhalation flow is greater than 45 and less than or equal to 200 liters per minute, the inhalation event is classified as a "good inhalation". If the peak inhalation flow is greater than 30 and less than or equal to 45 liters per minute, the inhalation event is classified as "fair". If the peak inhalation flow is above 200 liters per minute, the inhalation event is classified as a "possible air vent block" or an "excessive inhalation event", as previously described.

The inhalation event may be classified as an "exhalation", which may be sensed by airflow being detected in the opposite direction to that expected for inhalation using the inhaler 100.

In a non-limiting example, the inhaler is configured such that, for a normal inhalation, the medicament is dispensed approximately 0.5 seconds following the start of the inhalation. A subject's inhalation only reaching peak inhalation flow after the 0.5 seconds have elapsed, such as after approximately 1.5 seconds, may be partially indicative of the subject having difficulty in controlling their respiratory disease. Such a time to reach peak inhalation flow may, for example, be indicative of the subject facing an impending exacerbation.

More generally, the use determination system 12 may employ respective sensors (e.g. respective pressure sensors) for registering an inhalation/use of the inhaler and detecting the inhalation parameter, or a common sensor (e.g. a common pressure sensor) which is configured to fulfill both inhalation/use registering and inhalation parameter detecting functions.

Any suitable sensor may be included in the use determination system 12, such as one or more pressure sensors, temperature sensors, humidity sensors, orientation sensors, acoustic sensors, and/or optical sensors. The pressure sensor(s) may include a barometric pressure sensor (e.g. an atmospheric pressure sensor), a differential pressure sensor, an absolute pressure sensor, and/or the like. The sensors may employ microelectromechanical systems (MEMS) and/or nanoelectromechanical systems (NEMS) technology.

In a non-limiting example, the use determination system 12 comprises a differential pressure sensor.

The differential pressure sensor may, for instance, comprise a dual port type sensor for measuring a pressure difference across a section of the air passage through which the subject inhales. A single port gauge type sensor may alternatively be used. The latter operates by measuring the difference in pressure in the air passage during inhalation and when there is no flow. The difference in the readings corresponds to the pressure drop associated with inhalation.

In another non-limiting example, the use determination system 12 includes an acoustic sensor. The acoustic sensor in this example is configured to sense a noise generated when the subject inhales through the respective inhaler 100.

The acoustic sensor may include, for example, a microphone. The respective inhaler 100 may, for instance, comprise a capsule which is arranged to spin when the subject inhales though the device; the spinning of the capsule generating the noise for detection by the acoustic sensor. The spinning of the capsule may thus provide a suitably interpretable noise, e.g. rattle, for deriving use and/or inhalation parameter data.

An algorithm may, for example, be used to interpret the acoustic data in order to determine use data and/or the parameter relating to airflow during the inhalation. For instance, an algorithm as described by P. Colthorpe et al., "Adding Electronics to the Breezhaler: Satisfying the Needs of Patients and Regulators", Respiratory Drug Delivery 2018, 1, 71-80 may be used. Once the generated sound is detected, the algorithm may process the raw acoustic data to generate the use and/or inhalation parameter data.

Figure 3:
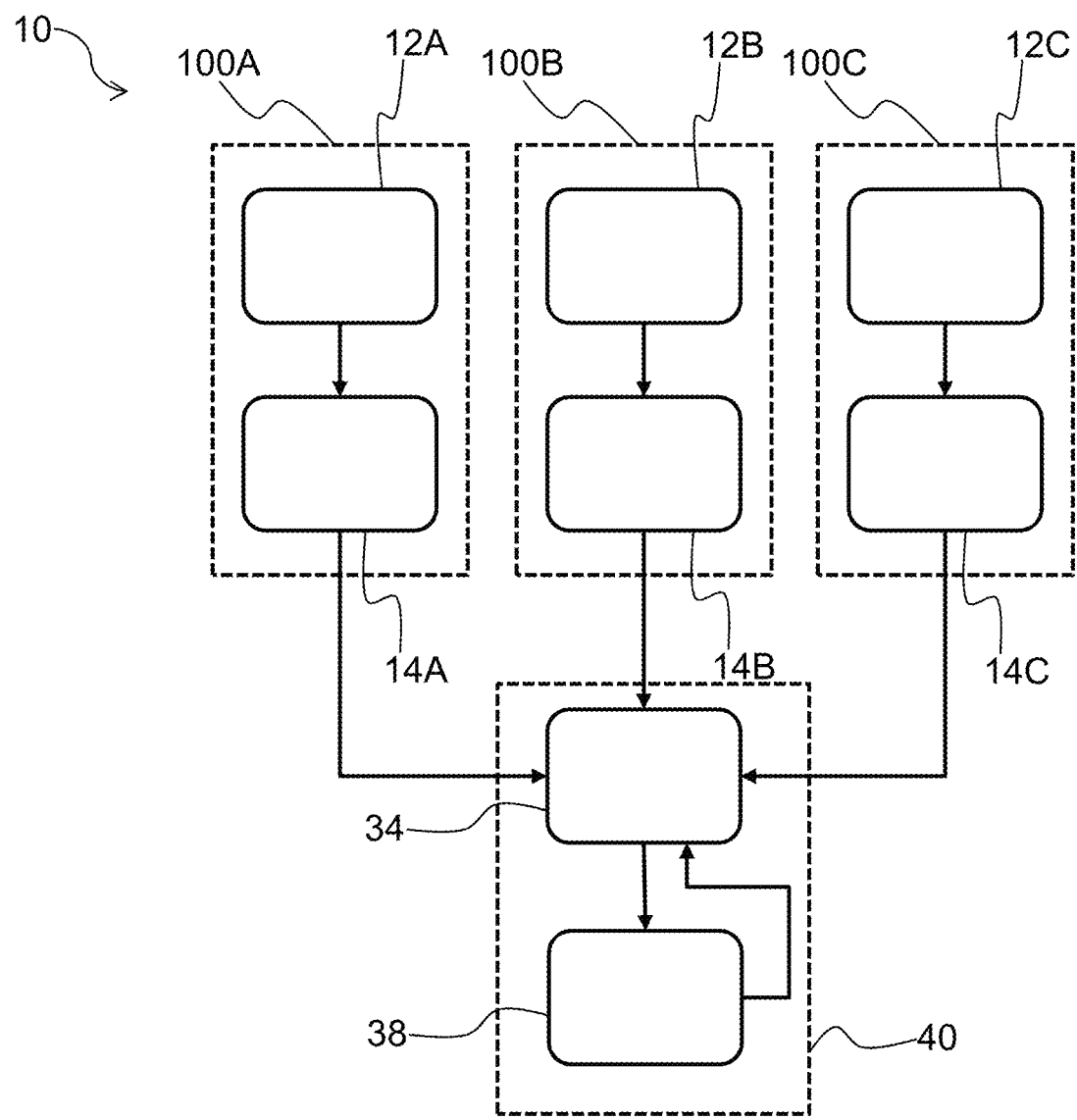
FIG. 3 shows a block diagram of a system according to an example.

FIG. 3 shows a block diagram of a system 10 according to a non-limiting example. The system 10 may, for example, be alternatively termed "an inhaler assembly".

As shown in FIG. 3, the system 10 comprises a first inhaler 100A comprising a first use determination system 12A, and a first transmission module 14A. This exemplary system 10 further comprises a second inhaler 100B comprising a second use determination system 12B, and a second transmission module 14B. The first inhaler 100A delivers a first medicament, and the second inhaler 100B delivers a second medicament which is different from the first medicament.

The exemplary system 10 depicted in FIG. 3 further comprises a third inhaler 100C comprising a third use determination system 12C, and a third transmission module 14C. The third inhaler 100C delivers a third medicament which is different from the first and second medicaments. In other examples, no third inhaler 100C is included in the system 10, or a fourth, fifth, etc. inhaler (not visible) is included in addition to the first inhaler 100A, the second inhaler 100B, and the third inhaler 100C. Alternatively or additionally, the system 10 includes a plurality of first inhalers 100A, a plurality of second inhalers 100B, and so on.

The system 10 comprises a processing module 34 which is configured to receive the respective encrypted data transmitted from one or more, e.g. each, of the transmission modules 14A, 14B, 14C, as represented in FIG. 3 by the arrows between each of the blocks corresponding to the transmission modules 14A, 14B, 14C and the block corresponding to the processing module 34. The first, second, and/or third encrypted data may be transmitted wirelessly to the processing module 34, as previously described. The processing module 34 may thus comprise a suitable receiver or transceiver for receiving the encrypted data. The receiver or transceiver of processing module 34 may be configured to implement the same communication protocols as transmission modules 14A, 14B, 14C and may thus include similar communication hardware and software as transmission modules 14A, 14B, 14C as described herein (not shown in FIG. 3).

Bluetooth communications between one or more, e.g. each, of the inhaler(s) 100A, 100B, 100C and the processing module 34 may enable relatively rapid transmission of the data from the former to the latter. For example, the longest time taken for the data to be transmitted to the processing module 34 may be around 3 minutes when the respective inhaler 100A, 100B, 100C is in Bluetooth range of the processing module 34.

The processing module 34 may comprise a suitable processor and memory configured to perform the functions described herein for the processing module. For example, the processor may be a general purpose processor programmed with computer executable instructions for implementing the functions of the processing module. The processor may be implemented using a microprocessor or microcontroller configured to perform the functions of the processing module. The processor may be implemented using an embedded processor or digital signal processor configured to perform the functions of the processing module. In an example, the processor may be implemented on a smartphone or other consumer electronic device that is capable of communicating with transmission modules 14A, 14B, 14C and performing the functions of the processing module 34 as described herein. For example, the processing module may be implemented on a smart phone or consumer electronic device that includes an application (e.g. app) that causes the processor of the smartphone or other consumer electronic device to perform the functions of the processing module 34 as described herein.

The processing module 34 distinguishes between the first encrypted data, the second encrypted data, and the third encrypted data, for example by using respective identifiers. In this manner, the respective parameters received from each of the inhalers 100A, 100B, 100C may be processed separately by the processing module so that inhalation information from one of the inhalers 100A, 100B, 100C is not conflated with inhalation information received from another of the inhalers 100A, 100B, 100C.

The system 10 further comprises a user interface 38. The processing module 34 is configured to control the user interface 38 to issue the above-described notification that the inhalation information derived from use(s) of the inhaler(s) 100A, 100B, 100C is available. This inhalation information may, for instance, be caused to be displayed via the user interface 38 by the user/subject inputting a request, e.g. by tapping an area of a touchscreen on which the notification is displayed, to view the inhalation information. The notification may be delivered/issued to the subject at the notification time, which notification time is delayed relative to the time assigned to the use, e.g. each use, of the respective inhaler 100A, 100B, 100C to which the inhalation information relates, as previously described.

In an embodiment, the user interface 38 is configured to, independently of the notification that the inhalation information is available, enable the user/subject to access the inhalation information relating to a use or attempted use of the inhaler. This may be by the user pushing buttons and/or accessing particular pages of an application in order to access the inhalation information.

The processing module may, in some examples, control the user interface to issue a confirmation that a use or attempted use of the inhaler has been determined by the use determination system. Such a confirmation may not, however, notify the subject/user that the inhalation information is available. In this respect, the notification that the inhalation information is available may be issued after such a confirmation.

In a non-limiting example, the confirmation that a use or attempted use of the inhaler has been determined, e.g. via the mouthpiece cover 108 having being opened then closed, may be issued within 15 minutes of the event. Such a confirmation may, for instance, read "We received your event". The notification including the inhalation information relating to the event may follow later, following implementation of the deliberate time delay.

For example, the notification that the inhalation information is available may be sent the day after the day on which the use has taken place and the confirmation issued to the user/subject.

The arrow pointing from the block representing the processing module 34 to the block representing the user interface 38 is intended to represent the control signal(s) which cause or causes the user interface 38 to issue the notification that the inhalation information is available. In this respect, the user interface 38 may comprise any suitable display, screen, for example touchscreen, etc. which is capable of displaying the inhalation information. Alternatively or additionally, the respective usage information may be provided by the user interface 38 via an audio message. In such an example, the user interface 38 comprises a suitable loudspeaker for delivering the audio message. Numerous ways of communicating the respective usage information can be used.

The notification may, for example, include a particular sound, text, and/or symbol which communicates to the subject/user that the inhalation information is available.

In a non-limiting example, a screen, e.g. a touchscreen, included in the user interface may be configured to, when in a locked state, provide the notification that the inhalation information is available, and when in an unlocked state following unlocking of the screen by the user, e.g. by input of a pin code, successful biometric recognition, etc., the inhalation information may be displayed or may at least be accessible by the subject/user.

By requiring the screen to be unlocked in this manner in order that the inhalation information can be communicated, the subject's/user's inhalation information may be prevented from being unintentionally displayed to someone other than the subject/user.

The notification may, for example, comprise a message inviting the user to view the inhalation information relating to a previous use or uses (or attempted use or uses) of the inhaler. Such use(s)/attempted use(s) of the inhaler may, for example, be from the day before the notification is issued, as previously described. Unlocking the screen and/or selecting, e.g. tapping on, the notification may cause the user interface to display a data page on which the inhalation information is provided.

In other examples, the inhalation information is included in the notification. The notification may, for instance, be displayed on a screen included in the user interface, with or without the screen having to be unlocked in order to view the inhalation information.

In yet another example, the system is configured such that the user is permitted to select whether or not screen unlocking is required in order for the user to view the inhalation information to which the notification relates.

Whilst the transmission modules 14A, 14B, 14C are each shown in FIG. 3 as transmitting (encrypted) data to the processing module 34, this is not intended to exclude the respective inhalers 100A, 1008, 100C, or a component module thereof, receiving data transmitted from the processing module 34.

In a non-limiting example, a clock module (not visible in the Figures) is included in each of the respective inhalers 100A, 100B, 100C for assigning a time, for example a time-and-date stamp, to the respective parameter.

Whilst not shown in FIG. 3, the processing module 34 may, in some examples, comprise a further clock module. The clock modules of each of the respective inhalers 100A, 100B, 100C may thus be synchronized according to the time provided by the further clock module. The further clock module may, for instance, receive the time of the time zone in which the processing module 34 is situated. This may cause the respective inhalers 100A, 100B, 100C to be synchronized according to the time in which the subject and their respective inhalers 100A, 100B, 100C are located, as previously described.

In such an example, the processing module 34 may be configured to synchronize the clock modules of the respective inhalers 100A, 100B, 100C. Such synchronization may, for instance, enable the notification time to be on a day which is subsequent to the day included in a time-and-date stamp assigned to the use of the respective inhaler 100A, 100B, 100C, as previously described.

Moreover, such synchronization may, for instance, provide a point of reference which enables the relative timing of use of the respective inhalers 100A, 100B, 100C to be determined, which may have clinical relevance. For example, such synchronization may permit a correlation to be drawn between failure of the subject to administer a maintenance medicament at regular times and increased rescue inhaler usage during the same period.

In an embodiment, the processing module 34 is at least partly included in a first processing module included in the user device 40. By implementing as much processing as possible of the usage data from the respective inhalers 100A, 100B, 100C in the first processing module of the user device 40, battery life in the respective inhalers 100A, 100B, 100C may be advantageously saved. The user device 40 may be, for example, at least one selected from a personal computer, a tablet computer, and a smart phone.

Alternatively or additionally, the user interface 38 may be at least partly defined by a first user interface of the user device 40. The first user interface of the user device 40 may, for instance, comprise, or be defined by, the touchscreen of a smart phone 40.

In other non-limiting examples, the processing module is not included in a user device. The processing module 34 (or at least part of the processing module 34) may, for example, be provided in a server, e.g. a remote server.

In a non-limiting example, the processing module 34 is configured to determine on a given day whether or not a use occurred on the previous day. If the processing module 34 determines that such a use, as determined by the use determination system 12, occurred on the previous day, the processing module 34 is configured to control the user interface 38 to issue, on said given day, the notification that the inhalation information is available. This protocol entails delaying the notification to the day after the use has taken place.

In a particular example, if the medicament delivered by the inhaler 100 is a maintenance medicament, such as fluticasone (propionate or furoate) or salmeterol (xinafoate) combined with fluticasone (propionate or furoate), and the processing module 34 determines that no such use occurred on the previous day, the processing module 34 is configured to control the user interface 38 to issue a synchronization request which requests the user to check and/or remedy the communication link between the inhaler 100 and the processing module 34.

In examples in which a transmission module 14 of the inhaler 100 wirelessly communicates with the processing module 34, the synchronization request comprises a request for the user to bring the inhaler 100 into wireless communications range of the processing module 34, e.g. within Bluetooth® range of the processing module 34.

In this way, an initial determination by the processing module 34 that no uses of the inhaler 100 delivering the maintenance medicament took place the previous day can lead to the processing module 34 obtaining data which confirms whether or not a use (or uses) actually took place the previous day.

Further, it should be appreciated that in some examples, the clock module may operate as an internal counter. When operating as an internal counter, the clock module may provide a relative count (e.g., as opposed to providing a mean solar time, such as a local mean time). For instance, the use determination system of an inhaler 100A, 100B, 100C may start an internal counter (e.g., which counts up from 0 indefinitely) when, for example, the use determination system is woken out of an energy-saving sleep mode for the first time (e.g., after the mouthpiece cover is opened for the first time).

Thereafter, any time-and-date stamp generated by the use determination system may be a relative time (or count) based on the internal counter of the clock module. The controller may periodically update the system clock every 250 microseconds (μs).

In instances where the clock module operates as an internal counter, a deliberate time delay for a notification may be determined using this relative count. For example, the user determination system of an inhaler 100A, 100B, 100C may assign a relative count as the time assigned to a use of the inhaler 100A, 100B, 100C by the subject, and may determine a deliberate time delay for a notification using this relative count. Alternatively or additionally, the use determination system of an inhaler 100A, 100B, 100C may send the relative count associated with a use of the inhaler 100A, 100B, 100C by the subject and the present count of the internal counter to the user device 40 and/or a server (e.g., to the processing module 34 residing on the user device 40 and/or the server), and the user device 40 and/or the server may be configured to determine a local mean time based on the time-and-date stamp indicating a relative count and the present count of the use determination system, and may be configured to determine a deliberate time delay for a notification using the local mean time.

Figure 4:
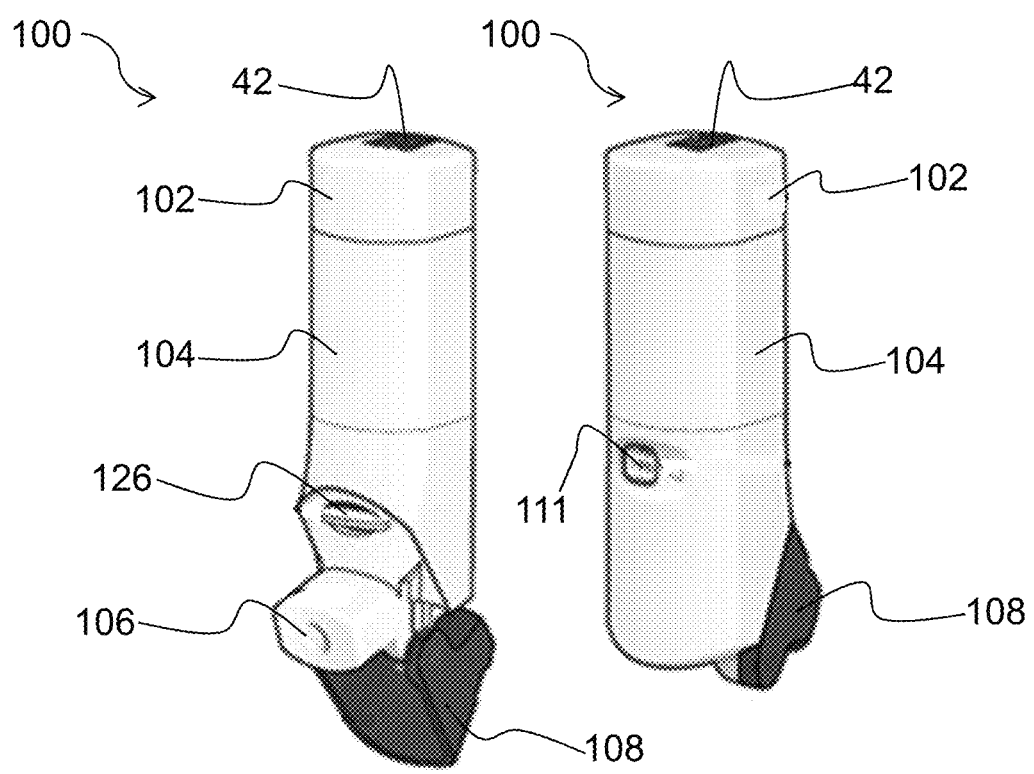
FIG. 4 shows front and rear views of the exterior of an inhaler according to an example.

FIG. 4 shows front and rear views of the exterior of an inhaler 100 according to a non-limiting example. The inhaler 100 comprises a top cap 102, a main housing 104, a mouthpiece 106, a mouthpiece cover 108, and an air vent 126. The mouthpiece cover 108 may be hinged to the main housing 104 so that it may open and close to expose the mouthpiece 106 and the air vent 126. The depicted inhaler 100 also comprises a mechanical dose counter 111, whose dose count may be used to check the number of doses remaining as determined by the processing module (on the basis of the total number of doses contained by the inhaler 100 prior to use and on the uses determined by the use determination system 12).

In the non-limiting example shown in FIG. 4, the inhaler 100 has a barcode 42 printed thereon. The barcode 42 in this example is a quick reference (QR) code printed on the uppermost surface of the top cap 102. The use determination system 12 and/or the transmission module 14 may, for example, be located at least partly within the top cap 102, for example as components of an electronics module (not visible in FIG. 4). The electronics module of the inhaler 100 will be described in greater detail with reference to FIGS. 12 to 15.

Figures 5, 6:
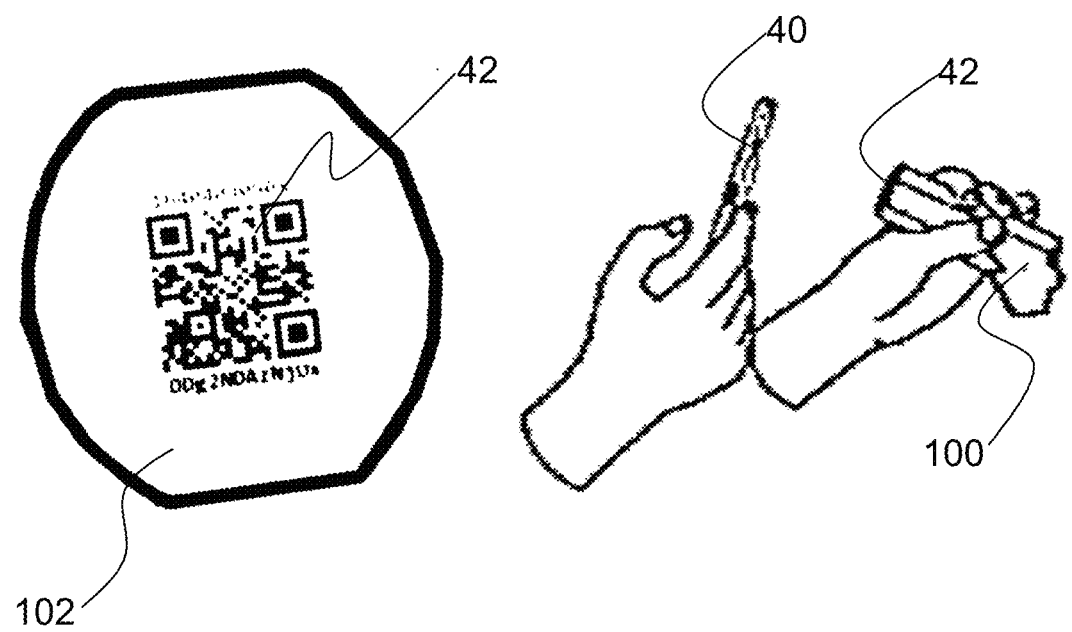
FIG. 5 shows an uppermost surface of the top cap of the inhaler shown in FIG. 4.
FIG. 6 schematically depicts pairing the inhaler shown in FIG. 4 with a user device.

The QR code is more clearly visible in FIG. 5, which provides a view from directly above the top cap 102 of the inhaler 100 shown in FIG. 4. The QR code 42 may provide a facile way of pairing the respective inhaler 100 with the processing module 34, in examples in which the user device 40 comprises a suitable optical reader, such as a camera, for reading the QR code. FIG. 6 shows a user pairing the inhaler 100 with the processing module 34 using the camera included in the user device 40, which in this particular example is a smart phone.

Such a bar code 42, e.g. QR code, may comprise the identifier which is assigned to the respective medicament of the inhaler 100, as previously described. Table 1 provides a non-limiting example of the identifiers included in the QR code 42 for various inhalers 100.

TABLE 1

| Identifier in QR code | Brand of inhaler | Medicament | Dose strength (mcg) | Total dose count of inhaler prior to use | Medicament identification number |
| --- | --- | --- | --- | --- | --- |
| <blank> | ProAir Digihaler | albuterol | 117 | 200 | AAA200 |
| AAA030 | ProAir Digihaler | albuterol | 117 | 30 | AAA030 |
| FSL060 | AirDuo Digihaler | fluticasone/ salmeterol | 55/14 | 60 | FSL060 |
| FSM060 | AirDuo Digihaler | fluticasone/ salmeterol | 113/14 | 60 | FSM060 |
| FSH060 | AirDuo Digihaler | fluticasone/ salmeterol | 232/14 | 60 | FSH060 |
| FPL060 | ArmonAir Digihaler | fluticasone | 55 | 60 | FPL060 |
| FPM060 | ArmonAir Digihaler | fluticasone | 113 | 60 | FPM060 |
| FPH060 | ArmonAir Digihaler | fluticasone | 232 | 60 | FPH060 |

As shown in Table 1, the identifier further denotes the dose strength and the total dose count of the inhaler prior to use. The processing module 34 may use the former to, in combination with the usage information, control the user interface 38 to issue a dosage notification when the label recommended dosages have been exceeded. Alternatively or additionally, the processing module 34 may use the total dose count of the inhaler prior to use and the usage information to determine the number of doses remaining in the respective inhaler 100, as previously described.

The barcode 42, e.g. QR code, on the inhaler may, for instance, further comprise a security key, for example in the form of a series of alphanumerical characters, for preventing unauthorized users from accessing the respective inhaler 100. The processing module 34 may be able to decrypt the respective encrypted data once the processing module 34 has been provided with the security key, but may not be able to decrypt the respective encrypted data before the processing module 34 has been provided with the security key. More generally, the security key may be included in the respective identifier.

In a non-limiting example, the system is configured to restrict one or more, e.g. each, of the inhalers included in the system to a single user account.

In such an example, a passkey, e.g. provided in the QR code, may allow synchronization between the respective inhaler and the processing module of the system. The passkey and, in turn, the usage parameter data, e.g. inhalation and/or usage data, from the respective inhaler may be public. This public inhalation data may not be associated with the particular subject until synchronization with the single user account.

Since the system is configured to restrict the respective inhaler to being associated with the single user account, the respective inhaler may be prevented from being synchronized with another user account, for example in situations where the inhaler is lost or stolen. In this way, third parties may be prevented from acquiring usage parameter data which is not theirs.

In other non-limiting examples, the processing module 34 may be paired with the respective inhaler 100 by, for example, manual entry of an alphanumerical key including the respective identifier via the user interface, e.g. a touchscreen.

In a non-limiting example, the processing module 34 determines a use and/or system error based on the parameter data, e.g. encrypted data, received from one or more, e.g. each, of the inhalers 100A, 100B, 100C included in the system 10. Such a use error may, for example, be indicative of potential misuse of the respective inhaler or inhalers 100A, 100B, 100C. The system error may be indicative of a fault with a component of the respective inhaler, such as the use determination system and/or the transmission module of the respective inhaler. A system error may, for example, include a hardware fault of the respective inhaler. The user interface 38 may be controlled by the processing module 34 to provide an alert or notification based on the determined use and/or system error.

Such a use error may, for example, be included in, or define, the inhalation information described above. In this respect, the use error may, for example, include a low inhalation event, a no inhalation event, and/or an excessive inhalation event.

A use error may alternatively or additionally include one or more of: the mouthpiece cover being left open for more than a predetermined time period, e.g. 60 seconds; multiple inhalations being recorded in respect of a single actuation of the above-described mechanical switch, for example a second inhalation performed within the same mouthpiece cover open/closed session; and an exhalation through the flow pathway, as determined from a positive pressure change being sensed in the flow pathway.

When the use error relates to the mouthpiece cover being left open for more than the predetermined time period, the inhalers detection circuitry may only stay active for the predetermined time period to preserve battery life. This may mean that anything which would otherwise be detectable/ determinable by the use determination system that occurs outside of this predetermined time period is not detected/ recorded. Notifying the user of this error may therefore serve the purpose of informing the user that otherwise detectable events are not detected outside the predetermined time period triggered by opening of the mouthpiece cover.

It is noted that the abovementioned exhalation-based use error may not be recorded if such an exhalation is sensed subsequently to an inhalation being performed in respect of a given actuation of the mechanical switch, e.g. within the same mouthpiece cover open/closed session.

System errors may include one or more of: a problem occurring when saving inhalation data to a memory included in the inhaler, such as a memory included in the use determination system ("corrupted data error"); an error with the clock module of the inhaler ("time stamp error"); and an error relating to collecting information about the inhalation ("inhalation parameter error").

In a particular example, use and/or system errors from more than one, e.g. all of, the inhalers included in the system are collected, e.g. aggregated, by the processing module. The processing module is further configured to control the user interface to provide the alert or notification based on the collected use and/or system errors. For instance, the processing module controls the user interface to provide the alert or notification based on the number of use and/or system errors collected from the inhalers included in the system reaching or exceeding a predetermined number of use and/or system errors.

Figure 7:
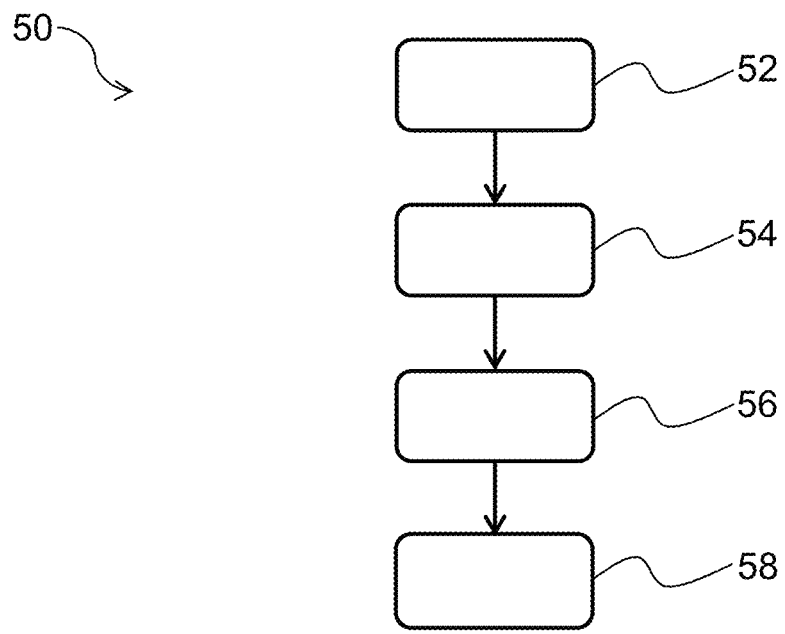
FIG. 7 provides a flowchart of a method according to an example.

FIG. 7 provides a flowchart of a method 50 according to an example. The method 50 comprises receiving 52 a parameter relating to airflow during a use of an inhaler by a subject; receiving 54 a time assigned to said use; determining 56 inhalation information from the parameter; and controlling 58 a user interface to issue a notification that the inhalation information is available at a notification time. The controlling comprises implementing a deliberate time delay which delays the notification time relative to the time assigned to the use.

This method 50 may, for example, be implemented by the processing module 34 of the system 10 described above. In some non-limiting examples, the method 50 is implemented by the processing module 34 residing on a user device, such as a smart phone or tablet.

Whilst FIG. 7 shows the determining 56 of the inhalation information from the parameter being implemented prior to the controlling 58 the user interface to issue the notification that the inhalation information is available, this is not intended to be limiting. The determining step 56 may alternatively be implemented after the controlling step 58, for instance in examples in which the notification does not itself include the inhalation information.

Further, in some examples, the method 50 comprises receiving 52 a parameter relating to a use of an inhaler by the subject. The parameter relating to use of the inhaler by the subject may include any combination of the actuation of a switch (e.g., which may be caused by movement of a mouthpiece cover of the inhaler 100 from a closed position to an open position), feedback from a sensor (e.g., a pressure sensor or acoustic sensor) indicating that airflow during a use of an inhaler by a subject exceeds a threshold indicative of use, and/or feedback from a sensor (e.g., an accelerometer) indicating that the inhaler is being handled by the user (e.g., the inhaler is being shaken for a predetermined amount of time, such as 5 seconds, or the inhaler is held a particular orientation suitable for operation for a predetermined amount of time, such as 10 seconds). The method may also include determining 54 a time assigned to said use; determining 56 feedback from the parameter; and controlling 58 a user interface to issue a notification that the inhalation information is available at a notification time, where the controlling comprises implementing a deliberate time delay which delays the notification time relative to the time assigned to the use. For example, the notification may include a "short shaking event" where the inhalation was shaken for less than a predetermined amount of time, an "improper orientation event" where the inhalation was not held in the proper orientation for the predetermined amount of time, or an "improper actuation event" where the user improperly operated the inhaler, for example, when attempting to meter a dose prior to inhalation.

Further, in some examples, the deliberate time delay may be different based on the type of event, for example, based on whether the event is categorized as a good inhalation event, a low inhalation event, a no inhalation event, an excessive inhalation event, a short duration inhalation event, a good duration inhalation event, a short shaking event, an improper orientation event, an improper actuation event, etc. As one non-limiting example, the deliberate time delay may be shorter when the inhalation event is categorized as a no inhalation event or an excessive inhalation event, as opposed to a low or good inhalation event. As another non-limiting example, the deliberate time delay may be shorter when the event is an improper actuation event as opposed to a low inhalation event or a short shaking event.

Figure 8:
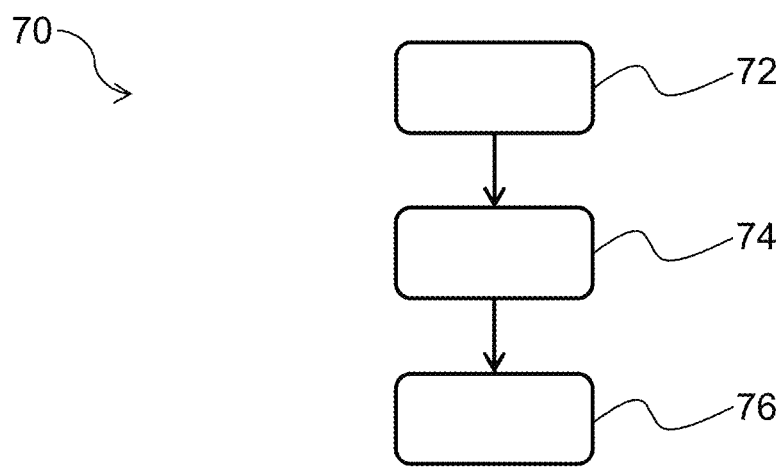
FIG. 8 provides a flowchart of a method according to another example.

As shown in FIG. 8, the present disclosure further provides a method 70 comprising adding 72 a further inhaler configured to dispense a medicament to a system comprising a processing module, a user interface, and an existing inhaler which is also configured to dispense the medicament. The further inhaler includes a (further) use determination system and a (further) transmission module, and the existing inhaler includes an existing use determination system and an existing transmission module. Such use determination systems and transmission modules have already been described above, so a further description here will be omitted for the sake of brevity only.

The method 70 comprises receiving 74 an identifier provided with the further inhaler, for example via a barcode, such as a QR code, printed on the further inhaler or its packaging, as previously described.

The identifier denotes at least the medicament and the dose strength of the medicament. The method further comprises using 76 the processing module to control the user interface to issue at least one medicament notification if the dose strength of the medicament in the further inhaler as denoted by the identifier is different from the dose strength of the medicament in the existing inhaler.

The at least one medicament notification may, for example, comprise a notification informing the subject that the dose strength of the further inhaler is different from that of the existing inhaler and/or a notification to request that the subject discards the existing inhaler. In this manner, the system may assist the subject to adjust to a prescription change.

The present disclosure further provides a method comprising determining whether a medicament of a further inhaler which is added to a system, which system comprises a processing module, a user interface, and an existing inhaler which delivers a maintenance medicament, is a further maintenance medicament.

The further inhaler includes a (further) use determination system and a (further) transmission module, and the existing inhaler includes an existing use determination system and an existing transmission module. Such use determination systems and transmission modules have already been described above, so a further description here will be omitted for the sake of brevity only.

The determination of whether the medicament is a further maintenance medicament may, for example, be based on an identifier which identifies that the further medicament is a maintenance medicament or is a different medicament type, such as a rescue medicament. The identifier may be received by the processing module of the system, and the processing module may implement the determination. Such an identifier may, for example, be included in a QR code of the further inhaler, as previously described.

If the medicament is identified as a further maintenance medicament, the method may further comprise controlling the user interface to prompt the user to select one of the existing inhaler and the further inhaler. Reminders may then be issued, e.g. by the processing module controlling the user interface to provide such reminders, according to the user selection to remind the subject to use the existing inhaler or the further inhaler according to a treatment regimen relating to administering of the maintenance medicament or the further maintenance medicament respectively.

In this manner, the method (or the system which is configured to implement the method) may limit such reminders to one maintenance inhaler. In other words, for instances where the subject is prescribed multiple maintenance inhalers, the user selection may cause the system to provide reminders for the selected maintenance inhaler, but not provide reminders for the maintenance inhaler which was not selected. The subject or user may select the particular maintenance inhaler based on the specific or current treatment regimen of the subject.

Alternatively or additionally, the method may comprise, based on the determination that the medicament is a further maintenance medicament, providing an alert, e.g. via the user interface and/or by transmitting a maintenance medicament notification to a healthcare provider, that the system comprises both the maintenance medicament and the further maintenance medicament.

Such an alert may, for example, comprise a message informing the user or subject to verify with their healthcare provider (and/or doctor) that a plurality of maintenance medicaments are prescribed for the subject.

Such an example may be applicable when, for instance, the subject is prescribed two maintenance medicaments at the same time, e.g. when the subject is transitioning between maintenance treatments. When the further inhaler is added to the system, for example when the QR code of the further inhaler is scanned, the processing module may be configured to provide the alert, e.g. by controlling the user interface and/or by transmitting the alert to the subject's healthcare provider.

Also provided is a computer program comprising computer program code which is adapted, when the computer program is run on a computer, to implement any of the above-described methods. In a preferred embodiment, the computer program takes the form of an app, for example an app for a user device 40, such as a mobile device, e.g. tablet computer or a smart phone.

Figure 9:
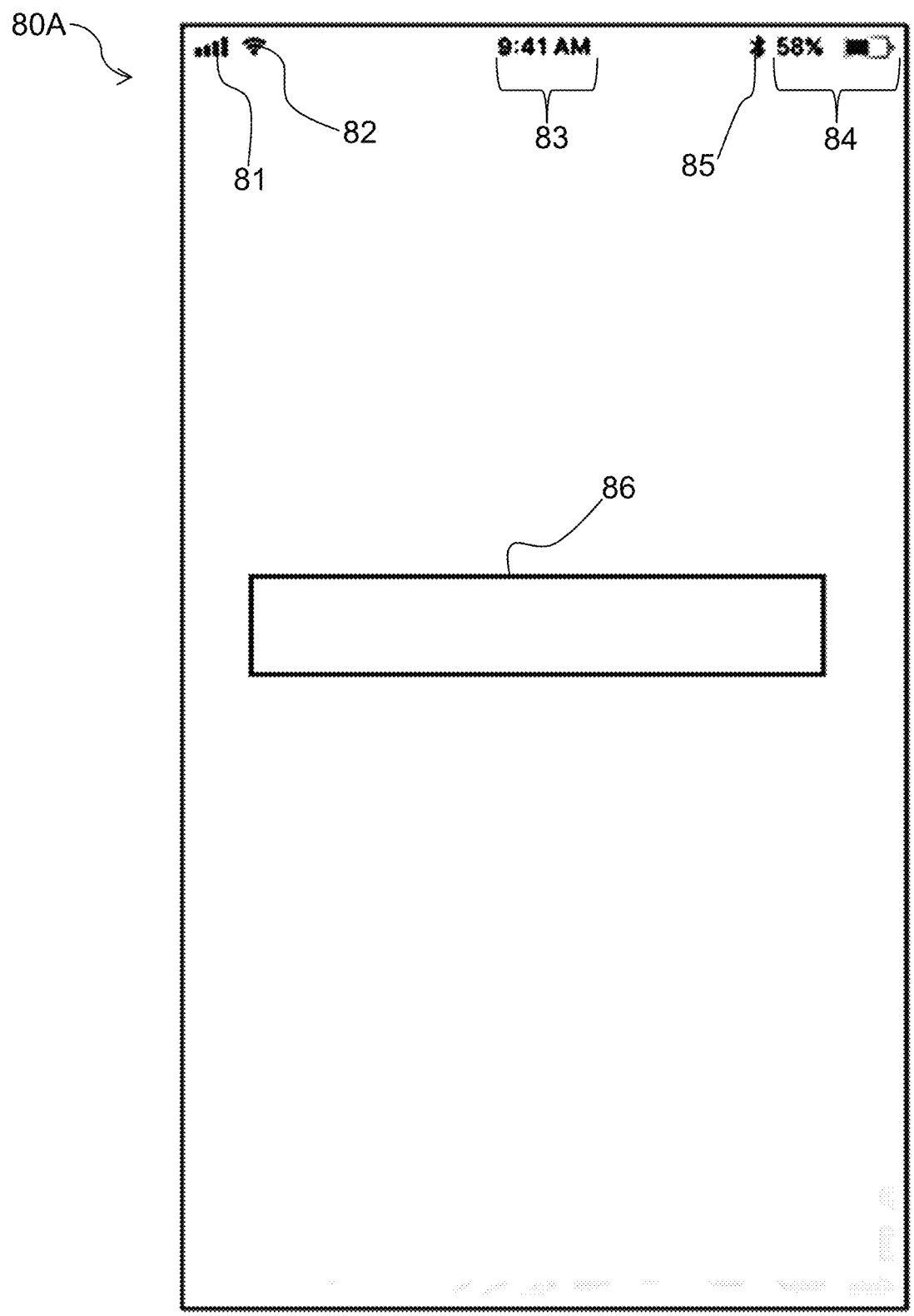
FIG. 9 provides a first view of a user interface according to an example.

FIG. 9 provides a first view of a user interface 38 according to a non-limiting example. In this example, the user interface 38 comprises the screen of a smart phone, which smart phone defines the user device 40. Symbol 81 denotes the signal strength of the cellular signal being received by the smart phone 40. Symbol 82 denotes that the smart phone 40 is connected to WiFi. The time 83 provided by the (further) clock module included in the processing module 34 of the smart phone 40. This time 83 may be used to synchronize the respective clock modules of the inhaler(s) 100A, 100B, 100C included in the system 10, as previously described.

The battery life 84 of the user device 40 is also displayed by the user interface 38. Symbol 85 indicates that Bluetooth® is enabled. At least one of the cellular signal 81, WiFi 82, and Bluetooth® 84 may be used to communicate with the respective inhaler 100A, 100B. Bluetooth® may be preferred.

The screenshot view 80A provided in FIG. 9 may be regarded as a "splash screen" which is presented while the app is being launched. Box 86 denotes the position of a logo relating to the respective inhaler 100A, 100B and/or app provider.

Figure 10:
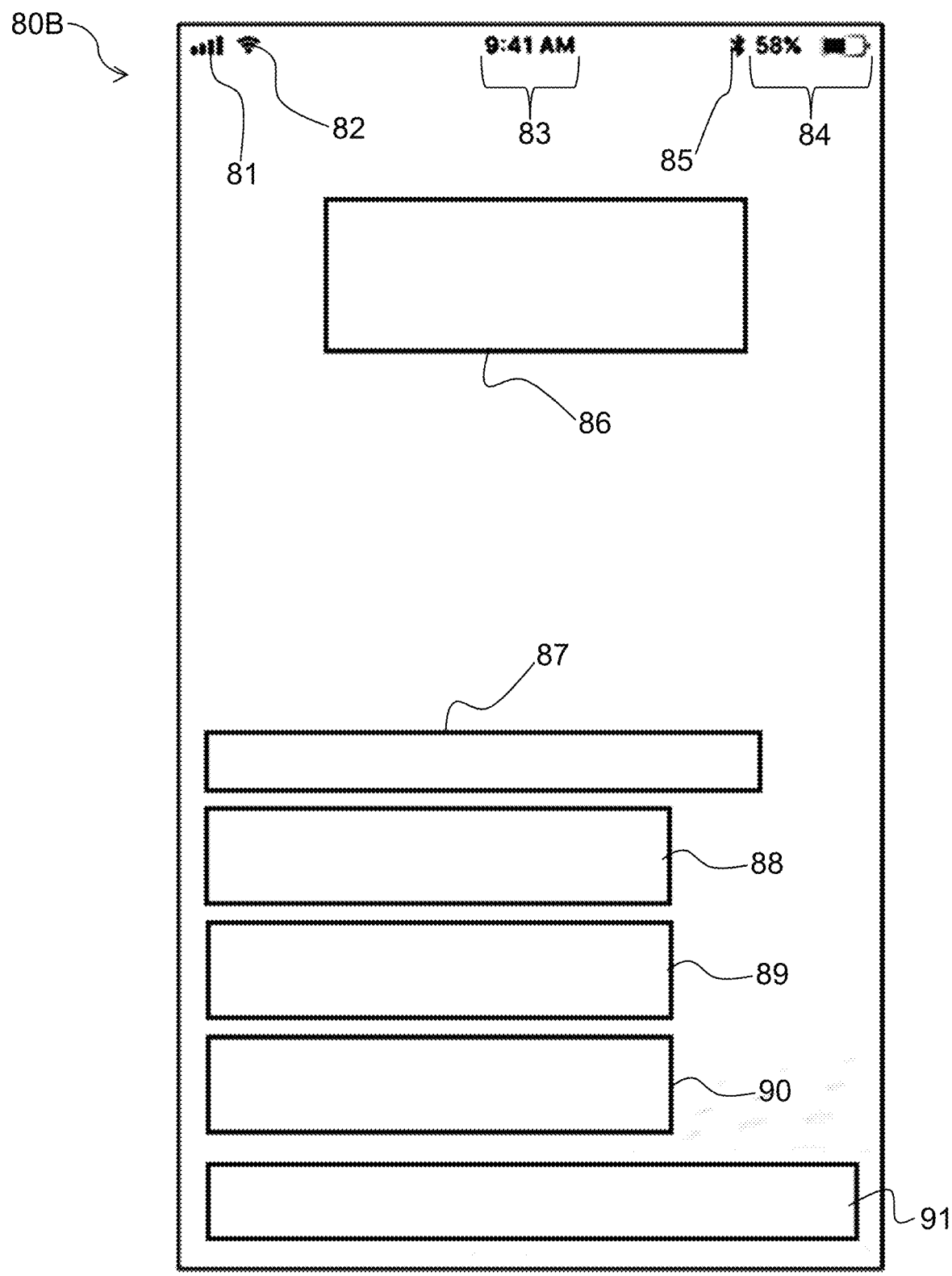
FIG. 10 provides a second view of a user interface according to an example.

FIG. 10 provides a second view 80B of the user interface 38. In this screenshot view 80B, the logo 86 is accompanied by details of the inhalers 100A, 100B, 100C supported by the app. Box 87 includes text and/or figures communicating that the app supports the inhalers 100A, 100B, 100C. Box 88 denotes the first inhaler 100A, box 89 denotes the second inhaler 100B, and box 90 denotes the third inhaler 100C, although the provision of more than one inhaler 100 is non-essential in the context of the present disclosure.

Box 91 provides a message for the subject to study safety information and full prescribing information in a relevant section of the app.

Figure 11:
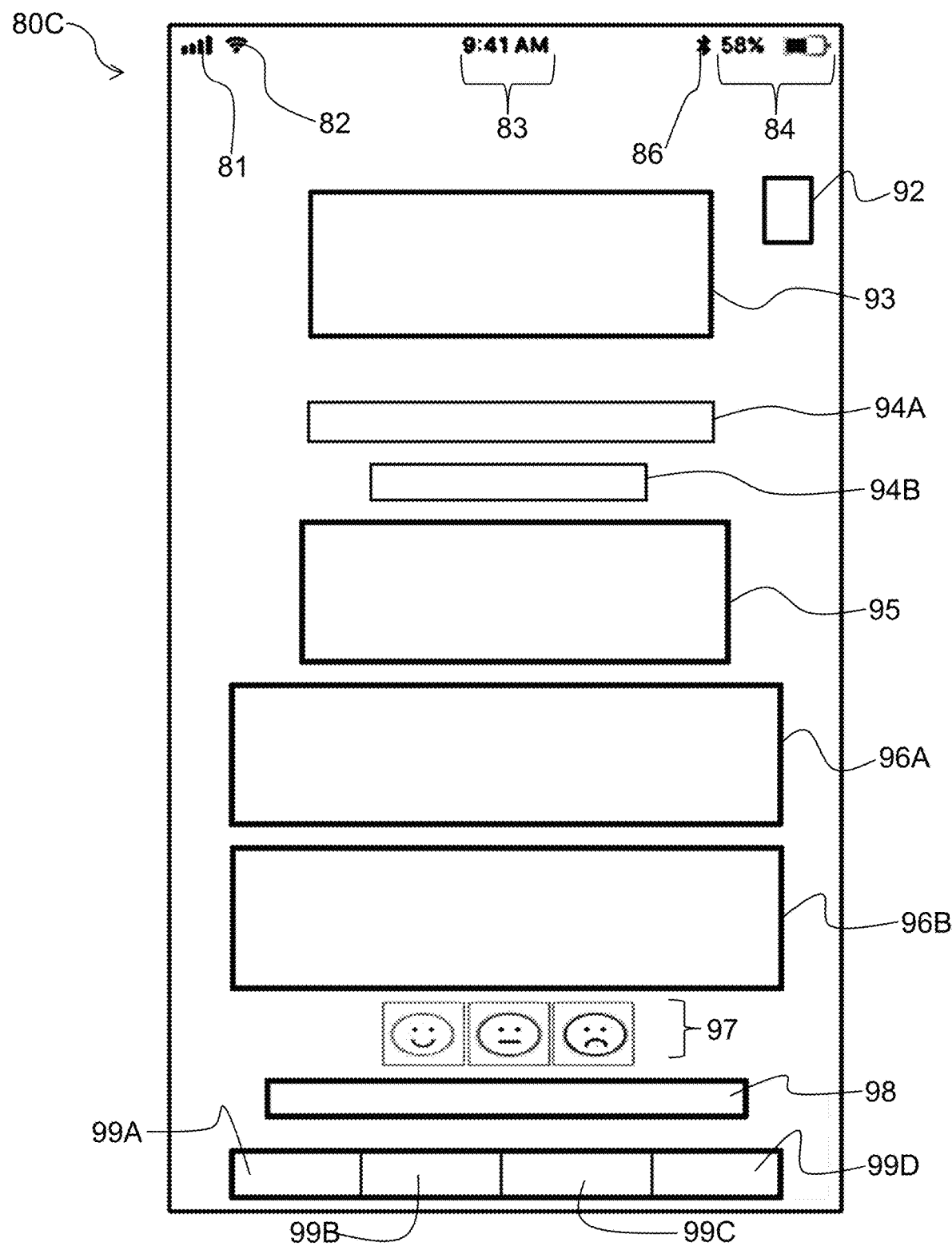
FIG. 11 provides a third view of a user interface according to an example.

FIG. 11 provides a third view of the user interface 38. This screenshot view 80C provides touch points and information relating to usage of the respective inhaler(s) 100A, 100B, 100C. Box 91 is a touchpoint which enables the subject to view the connectivity status, e.g. Bluetooth® connectivity status, of the respective inhaler(s) 100A, 100B, 100C.

Box 93 may provide an alert, reminder and/or notification. For instance, box 93 may contain a text or pictorial reminder for the subject to administer a maintenance medicament. One such notification may be, for example, the above-described notification that the inhalation information is available.

Box 94A may provide a salutation to the subject, for example using the time of the day associated with the time 83. Box 94B provides the date.

Box 95 provides environment information at the subject's location, such as weather, temperature, and/or humidity information. Such information may have relevance to the subject's management of their respiratory disease. The processing module 34 may be configured to retrieve such environment information, for example from a suitable third party internet source, and control the user interface 34 to display the retrieved environment information.

Box 96A provides first usage information relating to use of the first inhaler 100A. For example, the subject may be informed of registered uses of the first inhaler 100A during the day thus far, during the past 7 days, during the past 30 days, and so on. The box 96A may also provide a reminder to the subject to administer the first medicament at a certain point in the future.

Similarly, box 96B provides second usage information relating to use of the second inhaler 100B. The subject may, for example, be informed of registered uses of the second inhaler 100B during the day thus far, during the past 7 days, during the past 30 days, and so on.

The icons 97 in FIG. 11 enable the subject to input a self-assessment, for example a daily self-assessment, relating to how the subject is feeling, particularly in relation to the symptoms of the subject's respiratory disease. In this non-limiting example, the subject selects one of three emojitype icons according to how they are feeling that day. Box 98 is a touchpoint which is pressed by the subject to save their daily self-assessment.

The view 80C shown in FIG. 11 may be a home screen 99A, but tabs 99B, 99C, and 99D enable other screens to be accessed. Tab 99B enables the subject to access a data screen which provides further usage information, e.g. the above-described inhalation information, from the respective inhalers 100A, 100B, 100C. Tab 99C enables the subject to access a screen summarizing the inhalers 100A, 100B, 100C connected to the processing module 34. Tab 80C enables the subject to view their profile, which may contain personal data concerning the subject, such as name, date of birth, and so on.

FIGS. 12-15 provide a non-limiting example of an inhaler 100 which may be included in the system 10.

Figure 12:
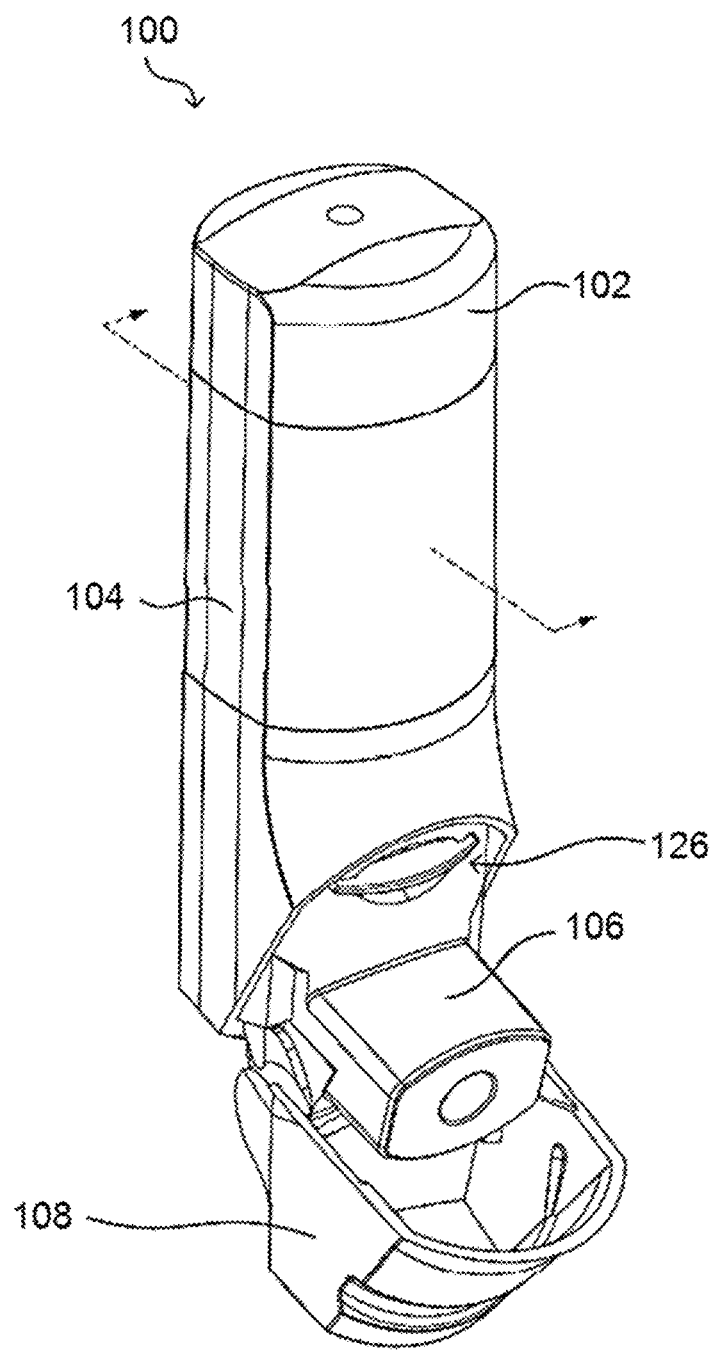
FIG. 12 shows a front perspective view of an exemplary inhaler.

FIG. 12 provides a front perspective view of an inhaler 100 according to a non-limiting example. The inhaler 100 may, for example, be a breath-actuated inhaler. The inhaler 100 may include a top cap 102, a main housing 104, a mouthpiece 106, a mouthpiece cover 108, an electronics module 120, and an air vent 126. The mouthpiece cover 108 may be hinged to the main housing 104 so that it may open and close to expose the mouthpiece 106. Although illustrated as a hinged connection, the mouthpiece cover 106 may be connected to the inhaler 100 through other types of connections. Moreover, while the electronics module 120 is illustrated as housed within the top cap 102 at the top of the main housing 104, the electronics module 120 may be integrated and/or housed within the main body 104 of the inhaler 100.

The electronics module 120 may, for instance, include the above-described use determination system 12 and the transmission module 14. For example, the electronics module 120 may include a processor, memory configured to perform the functions of use determination system 12 and/or transmission module 14. The electronics module 120 may include switch(es), sensor(s), slider(s), and/or other instruments or measurement devices configured to determine inhaler usage information as described herein. The electronics module 120 may include a transceiver and/or other communication chips or circuits configured to perform the transmission functions of transmission module 14.

Figure 13:
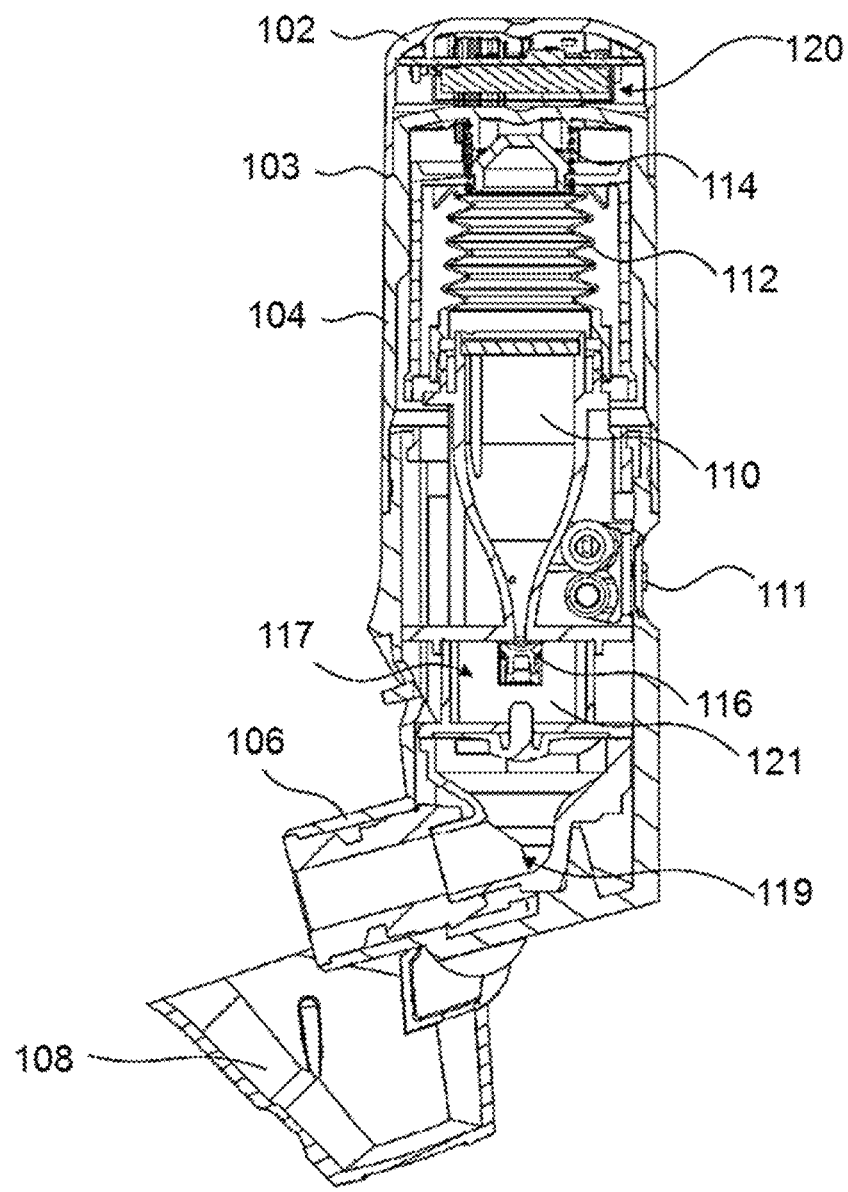
FIG. 13 shows a cross-sectional interior perspective view of the inhaler shown in FIG. 12.

FIG. 13 provides a cross-sectional interior perspective view of the example inhaler 100. Inside the main housing 104, the inhalation device 100 may include a medication reservoir 110 and a dose metering assembly. For example, the inhaler 100 may include a medication reservoir 110 (e.g. a hopper), a bellows 112, a bellows spring 114, a yoke (not visible), a dosing cup 116, a dosing chamber 117, a deagglomerator 121, and a flow pathway 119. The medication reservoir 110 may include medication, such as dry powder medication, for delivery to the subject. Although illustrated as a combination of the bellows 112, the bellows spring 114, the yoke, the dosing cup 116, the dosing chamber 117, and the deagglomerator 121, the dose metering assembly may include a subset of the components described and/or the inhalation device 100 may include a different dose metering assembly (e.g., based on the type of inhalation device, the type of medication, etc.). For instance, in some examples the medication may be included in a blister strip and the dose metering assembly, which may include one or more wheels, levers, and/or actuators, is configured to advance the blister strip, open a new blister that includes a dose of medication, and make that dose of medication available to a dosing chamber and/or mouthpiece for inhalation by the user.

When the mouthpiece cover 108 is moved from the closed to the open position, the dose metering assembly of the inhaler 100 may prime a dose of medicament. In the illustrated example of FIG. 13, the mouthpiece cover 108 being moved from the closed to the open position may cause the bellows 112 to compress to deliver a dose of medication from the medication reservoir 110 to the dosing cup 116. Thereafter, a subject may inhale through the mouthpiece 106 in an effort to receive the dose of medication.

The airflow generated from the subject's inhalation may cause the deagglomerator 121 to aerosolize the dose of medication by breaking down the agglomerates of the medicament in the dose cup 116. The deagglomerator 121 may be configured to aerosolize the medication when the airflow through the flow pathway 119 meets or exceeds a particular rate, or is within a specific range. When aerosolized, the dose of medication may travel from the dosing cup 116, into the dosing chamber 117, through the flow pathway 119, and out of the mouthpiece 106 to the subject. If the airflow through the flow pathway 119 does not meet or exceed a particular rate, or is not within a specific range, the medication may remain in the dosing cup 116. In the event that the medication in the dosing cup 116 has not been aerosolized by the deagglomerator 121, another dose of medication may not be delivered from the medication reservoir 110 when the mouthpiece cover 108 is subsequently opened. Thus, a single dose of medication may remain in the dosing cup until the dose has been aerosolized by the deagglomerator 121. When a dose of medication is delivered, a dose confirmation may be stored in memory at the inhaler 100 as dose confirmation information.

As the subject inhales through the mouthpiece 106, air may enter the air vent to provide a flow of air for delivery of the medication to the subject. The flow pathway 119 may extend from the dosing chamber 117 to the end of the mouthpiece 106, and include the dosing chamber 117 and the internal portions of the mouthpiece 106. The dosing cup 116 may reside within or adjacent to the dosing chamber 117. Further, the inhaler 100 may include a dose counter 111 that is configured to be initially set to a number of total doses of medication within the medication reservoir 110 and to decrease by one each time the mouthpiece cover 108 is moved from the closed position to the open position.

The top cap 102 may be attached to the main housing 104. For example, the top cap 102 may be attached to the main housing 104 through the use of one or more clips that engage recesses on the main housing 104. The top cap 102 may overlap a portion of the main housing 104 when connected, for example, such that a substantially pneumatic seal exists between the top cap 102 and the main housing 104.

Figure 14:
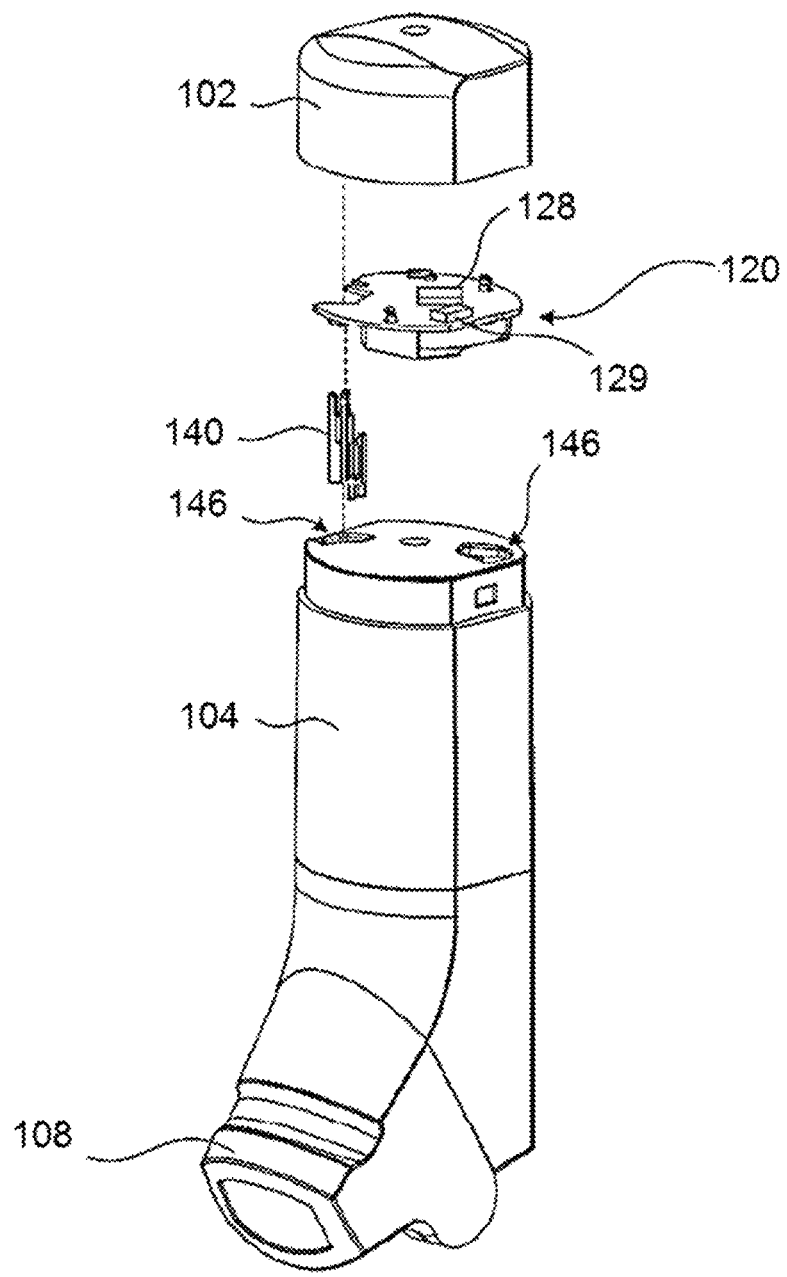
FIG. 14 provides an exploded perspective view of the example inhaler shown in FIG. 12.

FIG. 14 is an exploded perspective view of the example inhaler 100 with the top cap 102 removed to expose the electronics module 120. As shown in FIG. 20, the top surface of the main housing 104 may include one or more (e.g. two) orifices 146. One of the orifices 146 may be configured to accept a slider 140. For example, when the top cap 102 is attached to the main housing 104, the slider 140 may protrude through the top surface of the main housing 104 via one of the orifices 146.

Figure 15:
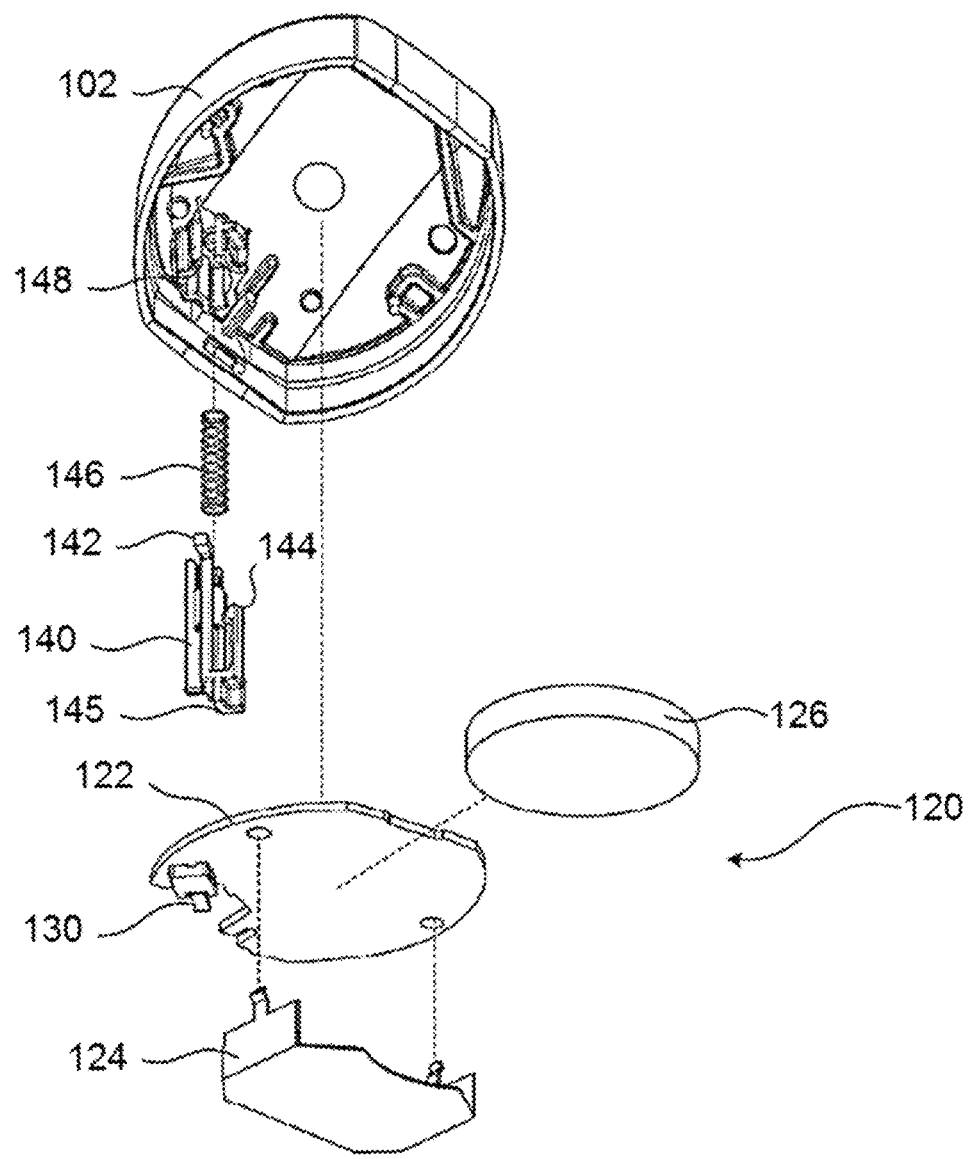
FIG. 15 provides an exploded perspective view of a top cap and electronics module of the inhaler shown in FIG. 12.

FIG. 15 is an exploded perspective view of the top cap 102 and the electronics module 120 of the example inhaler 100. As shown in FIG. 21, the slider 140 may define an arm 142, a stopper 144, and a distal end 145. The distal end 145 may be a bottom portion of the slider 140. The distal end 145 of the slider 140 may be configured to abut the yoke that resides within the main housing 104 (e.g. when the mouthpiece cover 108 is in the closed or partially open position).

The distal end 145 may be configured to abut a top surface of the yoke when the yoke is in any radial orientation. For example, the top surface of the yoke may include a plurality of apertures (not shown), and the distal end 145 of the slider 140 may be configured to abut the top surface of the yoke, for example, whether or not one of the apertures is in alignment with the slider 140.

The top cap 102 may include a slider guide 148 that is configured to receive a slider spring 146 and the slider 140. The slider spring 146 may reside within the slider guide 148. The slider spring 146 may engage an inner surface of the top cap 102, and the slider spring 146 may engage (e.g. abut) an upper portion (e.g. a proximate end) of the slider 140. When the slider 140 is installed within the slider guide 148, the slider spring 146 may be partially compressed between the top of the slider 140 and the inner surface of the top cap 102. For example, the slider spring 146 may be configured such that the distal end 145 of the slider 140 remains in contact with the yoke when the mouthpiece cover 108 is closed. The distal end 145 of the slider 145 may also remain in contact with the yoke while the mouthpiece cover 108 is being opened or closed. The stopper 144 of the slider 140 may engage a stopper of the slider guide 148, for example, such that the slider 140 is retained within the slider guide 148 through the opening and closing of the mouthpiece cover 108, and vice versa. The stopper 144 and the slider guide 148 may be configured to limit the vertical (e.g. axial) travel of the slider 140. This limit may be less than the vertical travel of the yoke. Thus, as the mouthpiece cover 108 is moved to a fully open position, the yoke may continue to move in a vertical direction towards the mouthpiece 106 but the stopper 144 may stop the vertical travel of the slider 140 such that the distal end 145 of the slider 140 may no longer be in contact with the yoke.

More generally, the yoke may be mechanically connected to the mouthpiece cover 108 and configured to move to compress the bellows spring 114 as the mouthpiece cover 108 is opened from the closed position and then release the compressed bellows spring 114 when the mouthpiece cover reaches the fully open position, thereby causing the bellows 112 to deliver the dose from the medication reservoir 110 to the dosing cup 116. The yoke may be in contact with the slider 140 when the mouthpiece cover 108 is in the closed position. The slider 140 may be arranged to be moved by the yoke as the mouthpiece cover 108 is opened from the closed position and separated from the yoke when the mouthpiece cover 108 reaches the fully open position. This arrangement may be regarded as a non-limiting example of the previously described dose metering assembly, since opening the mouthpiece cover 108 causes the metering of the dose of the medicament.

The movement of the slider 140 during the dose metering may cause the slider 140 to engage and actuate a switch 130. The switch 130 may trigger the electronics module 120 to register the dose metering. The slider 140 and switch 130 together with the electronics module 120 may thus be regarded as being included in the use determination system 12 described above. The slider 140 may be regarded in this example as the means by which the use determination system 12 is configured to register the metering of the dose by the dose metering assembly, each metering being thereby indicative of the inhalation performed by the subject using the inhaler 100.

Actuation of the switch 130 by the slider 140 may also, for example, cause the electronics module 120 to transition from the first power state to a second power state, and to sense an inhalation by the subject from the mouthpiece 106.

The electronics module 120 may include a printed circuit board (PCB) assembly 122, a switch 130, a power supply (e.g. a battery 126), and/or a battery holder 124. The PCB assembly 122 may include surface mounted components, such as a sensor system 128, a wireless communication circuit 129, the switch 130, and or one or more indicators (not shown), such as one or more light emitting diodes (LEDs). The electronics module 120 may include a controller (e.g. a processor) and/or memory. The controller and/or memory may be physically distinct components of the PCB 122. Alternatively, the controller and memory may be part of another chipset mounted on the PCB 122, for example, the wireless communication circuit 129 may include the controller and/or memory for the electronics module 120. The controller of the electronics module 120 may include a microcontroller, a programmable logic device (PLD), a microprocessor, an application specific integrated circuit (ASIC), a field programmable gate array (FPGA), or any suitable processing device or control circuit.

The controller may access information from, and store data in the memory. The memory may include any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The memory may be internal to the controller. The controller may also access data from, and store data in, memory that is not physically located within the electronics module 120, such as on a server or a smart phone.

The sensor system 128 may include one or more sensors. The sensor system 128 may be, for example, included in the use determination system 12 described above. The sensor system 128 may include one or more sensors, for example, of different types, such as, but not limited to one or more pressure sensors, temperature sensors, humidity sensors, orientation sensors, acoustic sensors, and/or optical sensors. The one or more pressure sensors may include a barometric pressure sensor (e.g. an atmospheric pressure sensor), a differential pressure sensor, an absolute pressure sensor, and/or the like. The sensors may employ microelectromechanical systems (MEMS) and/or nanoelectromechanical systems (NEMS) technology. The sensor system 128 may be configured to provide an instantaneous reading (e.g. pressure reading) to the controller of the electronics module 120 and/or aggregated readings (e.g. pressure readings) over time. As illustrated in FIGS. 13 and 14, the sensor system 128 may reside outside the flow pathway 119 of the inhaler 100, but may be pneumatically coupled to the flow pathway 119.

The controller of the electronics module 120 may receive signals corresponding to measurements from the sensor system 128. The controller may calculate or determine one or more airflow metrics using the signals received from the sensor system 128. The airflow metrics may be indicative of a profile of airflow through the flow pathway 119 of the inhaler 100. For example, if the sensor system 128 records a change in pressure of 0.3 kilopascals (kPa), the electronics module 120 may determine that the change corresponds to an airflow rate of approximately 45 liters per minute (Lpm) through the flow pathway 119.

Figure 16:
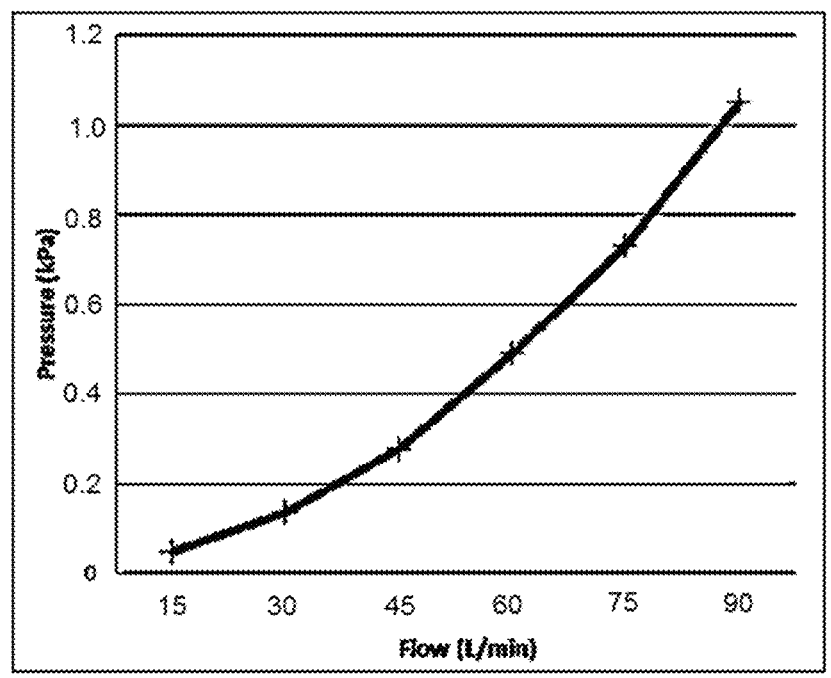
FIG. 16 shows a graph of airflow rate through the example inhaler shown in FIG. 12 versus pressure.

FIG. 16 shows a graph of airflow rates versus pressure. The airflow rates and profile shown in FIG. 16 are merely examples and the determined rates may depend on the size, shape, and design of the inhalation device 100 and its components.

The processing module 34 may generate personalized data in real-time by comparing signals received from the sensor system 128 and/or the determined airflow metrics to one or more thresholds or ranges, for example, as part of an assessment of how the inhaler 100 is being used and/or whether the use is likely to result in the delivery of a full dose of medication. For example, where the determined airflow metric corresponds to an inhalation with an airflow rate below a particular threshold, the processing module 34 may determine that there has been no inhalation or an insufficient inhalation from the mouthpiece 106 of the inhaler 100. If the determined airflow metric corresponds to an inhalation with an airflow rate above a particular threshold, the processing module 34 may determine that there has been an excessive inhalation from the mouthpiece 106. If the determined airflow metric corresponds to an inhalation with an airflow rate within a particular range, the processing module 34 may determine that the inhalation is "good", or likely to result in a full dose of medication being delivered.

The pressure measurement readings and/or the computed airflow metrics may be indicative of the quality or strength of inhalation from the inhaler 100. For example, when compared to a particular threshold or range of values, the readings and/or metrics may be used to categorize the inhalation as a certain type of event, such as a good inhalation event, a low inhalation event, a no inhalation event, or an excessive inhalation event. The categorization of the inhalation may be usage parameters stored as personalized data of the subject.

The no or low inhalation event may be associated with pressure measurement readings and/or airflow metrics below a particular threshold, such as an airflow rate less than or equal to 30 Lpm. The no inhalation event may occur when a subject does not inhale from the mouthpiece 106 after opening the mouthpiece cover 108 and during the measurement cycle. The no or low inhalation event may also occur when the subject's inspiratory effort is insufficient to ensure proper delivery of the medication via the flow pathway 119, such as when the inspiratory effort generates insufficient airflow to activate the deagglomerator 121 and, thus, aerosolize the medication in the dosing cup 116.

A fair inhalation event may be associated with pressure measurement readings and/or airflow metrics within a particular range, such as an airflow rate greater than 30 Lpm and less than or equal to 45 Lpm. The fair inhalation event may occur when the subject inhales from the mouthpiece 106 after opening the mouthpiece cover 108 and the subject's inspiratory effort causes at least a partial dose of the medication to be delivered via the flow pathway 119. That is, the inhalation may be sufficient to activate the deagglomerator 121 such that at least a portion of the medication is aerosolized from the dosing cup 116.

The good inhalation event may be associated with pressure measurement readings and/or airflow metrics above the low inhalation event, such as an airflow rate which is greater than 45 Lpm and less than or equal to 200 Lpm. The good inhalation event may occur when the subject inhales from the mouthpiece 106 after opening the mouthpiece cover 108 and the subject's inspiratory effort is sufficient to ensure proper delivery of the medication via the flow pathway 119, such as when the inspiratory effort generates sufficient airflow to activate the deagglomerator 121 and aerosolize a full dose of medication in the dosing cup 116.

The excessive inhalation event may be associated with pressure measurement readings and/or airflow metrics above the good inhalation event, such as an airflow rate above 200 Lpm. The excessive inhalation event may occur when the subject's inspiratory effort exceeds the normal operational parameters of the inhaler 100. The excessive inhalation event may also occur if the device 100 is not properly positioned or held during use, even if the subject's inspiratory effort is within a normal range. For example, the computed airflow rate may exceed 200 Lpm if the air vent is blocked or obstructed (e.g. by a finger or thumb) while the subject is inhaling from the mouthpiece 106.

Any suitable thresholds or ranges may be used to categorize a particular event. Some or all of the events may be used. For example, the no inhalation event may be associated with an airflow rate which is less than or equal to 45 Lpm and the good inhalation event may be associated with an airflow rate which is greater than 45 Lpm and less than or equal to 200 Lpm. As such, the low or fair inhalation event may not be used at all in some cases.

The pressure measurement readings and/or the computed airflow metrics may also be indicative of the direction of flow through the flow pathway 119 of the inhaler 100. For example, if the pressure measurement readings reflect a negative change in pressure, the readings may be indicative of air flowing out of the mouthpiece 106 via the flow pathway 119. If the pressure measurement readings reflect a positive change in pressure, the readings may be indicative of air flowing into the mouthpiece 106 via the flow pathway 119. Accordingly, the pressure measurement readings and/or airflow metrics may be used to determine whether a subject is exhaling into the mouthpiece 106, which may signal that the subject is not using the device 100 properly.

The inhaler 100 may include a spirometer or similarly operating device to enable measurement of lung function metrics. For example, the inhaler 100 may perform measurements to obtain metrics related to a subject's lung capacity. The spirometer or similarly operating device may measure the volume of air inhaled and/or exhaled by the subject. The spirometer or similarly operating device may use pressure transducers, ultrasound, or a water gauge to detect the changes in the volume of air inhaled and/or exhaled.

The personalized data collected from, or calculated based on, the usage of the inhaler 100 (e.g. pressure metrics, airflow metrics, lung function metrics, dose confirmation information, etc.) may be computed and/or assessed via external devices as well (e.g. partially or entirely). More specifically, the wireless communication circuit 129 in the electronics module 120 may include a transmitter and/or receiver (e.g. a transceiver), as well as additional circuitry. The wireless communication circuit 129 may include, or define, the transmission module 14 of the inhaler 100.

For example, the wireless communication circuit 129 may include a Bluetooth chip set (e.g. a Bluetooth Low Energy chip set), a ZigBee chipset, a Thread chipset, etc. As such, the electronics module 120 may wirelessly provide the personalized data, such as pressure measurements, airflow metrics, lung function metrics, dose confirmation information, and/or other conditions related to usage of the inhaler 100, to an external processing module 34, such as a processing module 34 included in a smart phone 40. The personalized data may be provided in real time to the external device to enable exacerbation risk prediction based on real-time data from the inhaler 100 that indicates time of use, how the inhaler 100 is being used, and personalized data about the subject, such as real-time data related to the subject's lung function and/or medical treatment. The external device may include software for processing the received information and for providing compliance and adherence feedback to the subject via a graphical user interface (GUI). The graphical user interface may be included in, or may define, the user interface 38 included in the system 10.

The airflow metrics may include personalized data that is collected from the inhaler 100 in real-time, such as one or more of an average flow of an inhalation/exhalation, a peak flow of an inhalation/exhalation (e.g. a maximum inhalation received), a volume of an inhalation/exhalation, a time to peak of an inhalation/exhalation, and/or the duration of an inhalation/exhalation. The airflow metrics may also be indicative of the direction of flow through the flow pathway 119. That is, a negative change in pressure may correspond to an inhalation from the mouthpiece 106, while a positive change in pressure may correspond to an exhalation into the mouthpiece 106. When calculating the airflow metrics, the electronics module 120 may be configured to eliminate or minimize any distortions caused by environmental conditions. For example, the electronics module 120 may re-zero to account for changes in atmospheric pressure before or after calculating the airflow metrics. The one or more pressure measurements and/or airflow metrics may be time-stamped and stored in the memory of the electronics module 120.

In addition to the airflow metrics, the inhaler 100, or another computing device, may use the airflow metrics to generate additional personalized data. For example, the controller of the electronics module 120 of the inhaler 100 and/or the processing module 34 may translate the airflow metrics into other metrics that indicate the subject's lung function and/or lung health that are understood to medical practitioners, such as peak inspiratory flow metrics, peak expiratory flow metrics, and/or forced expiratory volume in 1 second (FEV1), for example. The processing module 34 and/or the electronics module 120 of the inhaler 100 may determine a measure of the subject's lung function and/or lung health using a mathematical model such as a regression model. The mathematical model may identify a correlation between the total volume of an inhalation and FEV1. The mathematical model may identify a correlation between peak inspiratory flow and FEV1. The mathematical model may identify a correlation between the total volume of an inhalation and peak expiratory flow. The mathematical model may identify a correlation between peak inspiratory flow and peak expiratory flow.

The battery 126 may provide power to the components of the PCB 122. The battery 126 may be any suitable source for powering the electronics module 120, such as a coin cell battery, for example. The battery 126 may be rechargeable or non-rechargeable. The battery 126 may be housed by the battery holder 124. The battery holder 124 may be secured to the PCB 122 such that the battery 126 maintains continuous contact with the PCB 122 and/or is in electrical connection with the components of the PCB 122. The battery 126 may have a particular battery capacity that may affect the life of the battery 126. As will be further discussed below, the distribution of power from the battery 126 to the one or more components of the PCB 122 may be managed to ensure the battery 126 can power the electronics module 120 over the useful life of the inhaler 100 and/or the medication contained therein.

In a connected state, the communication circuit and memory may be powered on and the electronics module 120 may be "paired" with an external device, such as a smart phone. The controller may retrieve data from the memory and wirelessly transmit the data to the external device. The controller may retrieve and transmit the data currently stored in the memory. The controller may also retrieve and transmit a portion of the data currently stored in the memory. For example, the controller may be able to determine which portions have already been transmitted to the external device and then transmit the portion(s) that have not been previously transmitted. Alternatively, the external device may request specific data from the controller, such as any data that has been collected by the electronics module 120 after a particular time or after the last transmission to the external device. The controller may retrieve the specific data, if any, from the memory and transmit the specific data to the external device.

The data stored in the memory of the electronics module 120 (e.g. the signals generated by the switch 130, the pressure measurement readings taken by the sensory system 128 and/or the airflow metrics computed by the controller of the PCB 122) may be transmitted to an external device, which may process and analyze the data to determine the usage parameters associated with the inhaler 100. Further, a mobile application residing on the mobile device may generate feedback for the user based on data received from the electronics module 120. For example, the mobile application may generate daily, weekly, or monthly report, provide confirmation of error events or notifications, provide instructive feedback to the subject, and/or the like.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Embodiments. Below are non-limiting examples of various embodiments that are discussed herein.

1. A system comprising:
an inhaler comprising a use determination system configured to:
  determine a parameter relating to airflow during a use of the inhaler by a subject; and
  assign a time to the use;
a user interface; and
a processing module configured to:
  determine inhalation information from the parameter; and
  control the user interface to issue a notification at a notification time that the inhalation information is available, the processing module being configured to implement a deliberate time delay such that the notification time is delayed relative to the time assigned to the use.

2. The system according to claim 1, wherein the notification time is at least 5 minutes after the time assigned to the use.

3. The system according to claim 1 or claim 2, wherein the notification time is less than 48 hours after the time assigned to the use.

4. The system according to any of claims 1 to 3, wherein the use determination system is configured such that a time-and-date stamp is assigned to the use.

5. The system according to claim 4, wherein the notification time is a predetermined time on a day which is subsequent to the day included in the time-and-date stamp.

6. The system according to any of claims 1 to 5, wherein the use determination system comprises a sensor for detecting the parameter.

7. The system according to any of claims 1 to 6, wherein the use determination system comprises a mechanical switch configured to be actuated prior to, during, or after use of the inhaler; optionally wherein the inhaler comprises a mouthpiece through which the user performs the inhalation, and a mouthpiece cover, and wherein the mechanical switch is configured to be actuated when the mouthpiece cover is moved to expose the mouthpiece.

8. The system according to any of claims 1 to 7, wherein the inhalation information indicates one or more of:

a no inhalation event in which no inhalation is detected by the use determination system;

a low inhalation event in which an inhalation is detected by the use determination system, but a value relating to the airflow is equal to or lower than a first predetermined threshold;

an excessive inhalation event in which an inhalation is detected by the use determination system, but a value relating to the airflow is higher than a second predetermined threshold;

a fair inhalation event in which an inhalation is detected by the use determination system, and a value relating to the airflow is higher than the first predetermined threshold, lower than the second predetermined threshold, and equal to or lower than a third predetermined threshold, said third predetermined threshold being between the first and second predetermined thresholds; and a good inhalation event in which an inhalation is detected by the use determination system, and a value relating to the airflow is equal to or lower than the second predetermined threshold and higher than the third predetermined threshold.

9. The system according to claim 8, wherein the value relating to the airflow is a value of peak inhalation flow; optionally wherein the first predetermined threshold is 30 liters per minute, the second predetermined threshold is 200 liters per minute, and the third predetermined threshold is 45 liters per minute.

10. The system according to claim 8 or claim 9 as according to claim 7, wherein the no inhalation event is recorded when no inhalation is detected by the use determination system following a predetermined time elapsing following actuation of the mechanical switch.

11. The system according to any of claims 1 to 10, wherein the user interface is at least partly defined by a first user interface of a user device; optionally wherein the user device is at least one selected from a personal computer, a tablet computer, and a smart phone.

12. The system according to claim 11, wherein the processing module is at least partly included in a first processing module included in the user device.

13. The system according to any of claims 1 to 12, wherein the inhaler contains a medicament, the medicament being delivered to the user during the use of the inhaler; optionally wherein the medicament is selected from albuterol, budesonide, beclomethasone, fluticasone, formoterol, salmeterol, indacaterol, vilanterol, tiotropium, aclidinium, umeclidinium, glycopyrronium, salmeterol combined with fluticasone, beclomethasone combined with albuterol, and budesonide combined with formoterol.

14. A method comprising:

receiving a parameter relating to airflow during a use of an inhaler by a subject;

receiving a time assigned to said use;

determining inhalation information from the parameter; and controlling a user interface to issue a notification at a notification time that the inhalation information is available, wherein said controlling comprises implementing a deliberate time delay which delays the notification time relative to the time assigned to the use.

15. The method according to claim 14, wherein the notification time is at least 5 minutes after the time assigned to the use.

16. The method according to claim 14 or claim 15, wherein the notification time is less than 48 hours after the time assigned to the use.

17. The method according to any of claims 14 to 16, wherein a time-and-date stamp is assigned to the use.

18. The method according to claim 17, wherein the notification time is a predetermined time on a day which is subsequent to the day included in the time-and-date stamp.

19. The method according to any of claims 1 to 18, wherein the inhalation information indicates one or more of:

a no inhalation event in which no inhalation is detected during the use of the inhaler;

a low inhalation event in which an inhalation is detected during the use of the inhaler, but a value relating to the airflow is equal to or lower than a first predetermined threshold;

an excessive inhalation event in which an inhalation is detected during the use of the inhaler, but a value relating to the airflow is higher than a second predetermined threshold;

a fair inhalation event in which an inhalation is detected during the use of the inhaler, and a value relating to the airflow is higher than the first predetermined threshold, lower than the second predetermined threshold, and equal to or lower than a third predetermined threshold, said third predetermined threshold being between the first and second predetermined thresholds; and a good inhalation event in which an inhalation is detected during the use of the inhaler, and a value relating to the airflow is equal to or lower than the second predetermined threshold and higher than the third predetermined threshold.

20. The method according to claim 19, wherein the value relating to the airflow is a value of peak inhalation flow; optionally wherein the first predetermined threshold is 30 liters per minute, the second predetermined threshold is 200 liters per minute, and the third predetermined threshold is 45 liters per minute.

21. A computer program comprising computer program code which is adapted, when said computer program is run on a computer, to implement the method of any of claims 14 to 20.

What is claimed is:

1. A system comprising:

an external device comprising a processor, memory, and a transceiver; and an inhaler comprising a medicament, a processor, memory, and a transmitter, the processor of the inhaler configured to:

determine a parameter relating to airflow during a use of the inhaler by a subject;

assign a time to the use; and send, to the external device, the parameter relating to the airflow and the time of the use; and wherein the processor of the external device is configured to:
receive the parameter relating to airflow and the time of the use;
determine inhalation information from the parameter relating to airflow; and
control a user interface to issue a notification at a notification time that the inhalation information is available, the processor of the external device configured to implement a deliberate time delay such that the notification time is delayed relative to the time assigned to the use, and wherein the time delay is a shorter deliberate time delay when the use of the inhaler by the subject is categorized as a no inhalation event or an excessive inhalation event as opposed to a low inhalation event or a good inhalation event.

2. The system of claim 1, wherein the deliberate time delay is configured such that the notification time is at least 5 minutes after the time assigned to the use.

3. The system of claim 2, wherein the deliberate time delay is configured such that the notification time is less than 48 hours after the time assigned to the use.

4. The system of claim 1, wherein the processor of the external device is configured to assign a time-and-date stamp to the use based on the time of the use provided by the inhaler.

5. The system of claim 4, wherein the deliberate time delay is configured such that the notification time is a predetermined time on a day which is subsequent to the day included in the time-and-date stamp.

6. The system of claim 4, wherein the time to the use assigned by the inhaler is a relative count determined based on an internal counter of the inhaler, and wherein the external device of a server is configured to determine a local mean time based on the relative count.

7. The system of claim 1, wherein the inhaler comprises a mechanical switch configured to be actuated prior to, during, or after use of the inhaler; and
wherein the inhaler comprises a pressure sensor or an acoustic sensor for detecting the parameter.

8. The system of claim 7, wherein the inhaler comprises a mouthpiece through which the user performs an inhalation, and a mouthpiece cover, and wherein the mechanical switch is configured to be actuated when the mouthpiece cover is moved to expose the mouthpiece.

9. The system of claim 1, wherein the inhalation information indicates one or more of:
the no inhalation event in which no inhalation is detected by the processor of the inhaler;
the low inhalation event in which an inhalation is detected by the processor of the inhaler, but the parameter relating to the airflow is equal to or lower than a first predetermined threshold;
the excessive inhalation event in which an inhalation is detected by the processor of the inhaler, but the parameter relating to the airflow is higher than a second predetermined threshold;
a fair inhalation event in which an inhalation is detected by the processor of the inhaler, and the parameter relating to the airflow is higher than the first predetermined threshold, lower than the second predetermined threshold, and equal to or lower than a third predetermined threshold, said third predetermined threshold being between the first and second predetermined thresholds; or
the good inhalation event in which an inhalation is detected by the processor of the inhaler, and the parameter relating to the airflow is equal to or lower than the second predetermined threshold and higher than the third predetermined threshold.

10. The system of claim 9, wherein the parameter relating to the airflow is a value of peak inhalation flow, and wherein the first predetermined threshold is 30 liters per minute, the second predetermined threshold is 200 liters per minute, and the third predetermined threshold is 45 liters per minute.

11. The system of claim 9, wherein the no inhalation event is recorded when no inhalation is detected by the processor of the inhaler following a predetermined time elapsing following actuation of a mechanical switch of the inhaler, the mechanical switch being configured to be actuated prior to, during, or after use of the inhaler.

12. The system of claim 1, wherein the external device comprises a personal computer, a tablet computer, or a smart phone, and the user interface comprises a touch sensitive display screen of the external device.

13. The system of claim 1, wherein the inhalation information comprises a peak inhalation flow, an inhalation volume, a time to peak inhalation flow, or an inhalation duration of the airflow during the use of the inhaler.

14. The system of claim 1, wherein the inhalation information indicates an error message indicating that an air vent of the inhaler is blocked or obstructed during the use of the inhaler.

15. The system of claim 1, wherein the inhalation information indicates a use error that occurred during the use of the inhaler by the subject.

16. The system of claim 1, wherein the no inhalation event is characterized by no inhalation being detected by the processor of the inhaler, or is characterized by an inhalation being detected by the processor of the inhaler but the parameter relating to the airflow being equal to or less than a first threshold;
wherein the excessive inhalation event is characterized by an inhalation being detected by the processor of the inhaler but the parameter relating to the airflow being higher than a second threshold; and
wherein the good inhalation event is characterized by an inhalation being detected by the processor of the inhaler, and the parameter relating to the airflow being equal to or lower than the second predetermined threshold and higher than the first predetermined threshold.

17. The system of claim 1, wherein the medicament comprises a corticosteroid (ICS) or a bronchodilator.

18. The system of claim 1, wherein the medicament is a short-acting β2-agonist or a rapid-onset long-acting β2-agonist.

19. The system of claim 1, wherein the medicament is an ICS that comprises one or more of budesonide, beclomethasone (dipropionate), fluticasone (propionate or furoate), mometasone (furoate), ciclesonide, or dexamethasone (sodium).

20. The system of claim 1, wherein the medicament is selected from albuterol (sulfate), budesonide, beclomethasone (dipropionate), fluticasone (propionate or furoate), formoterol (fumarate), salmeterol (xinafoate), indacaterol (maleate), vilanterol (triphenylacetate), tiotropium (bromide), aclidinium (bromide), umeclidinium (bromide), glycopyrronium (bromide), salmeterol (xinafoate) combined with fluticasone (propionate or furoate), beclomethasone (dipropionate) combined with albuterol (sulfate), and budesonide combined with formoterol (fumarate).

21. The system of claim 1, wherein the medicament is a bronchodilator β2-adrenergic agonist that comprises one or more of formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride), vilanterol (triphenylacetate), albuterol (sulfate) or terbutaline (sulfate).

22. The system of claim 1, wherein the medicament is a bronchodilator anticholinergic that comprises one or more of tiotropium (bromide), oxitropium (bromide), aclidinium (bromide), umeclidinium (bromide),ipratropium (bromide) glycopyrronium (bromide), oxybutynin (hydrochloride or hydrobromide), tolterodine (tartrate), trospium (chloride), solifenacin (succinate), fesoterodine (fumarate), or darifenacin (hydrobromide).

23. A system comprising:
an external device comprising a processor, memory, and a transceiver; and
an inhaler comprising a processor, memory, and a transmitter, the processor of the inhaler configured to:
determine a parameter relating to airflow during a use of the inhaler by a subject;
assign a time to the use; and
send, to the external device, the parameter relating to the airflow and the time of the use; and
wherein the processor of the external device is configured to:
receive the parameter relating to airflow and the time of the use;
determine inhalation information from the parameter relating to airflow; and
control a user interface to issue a notification at a notification time that the inhalation information is available, the processor of the external device configured to implement a deliberate time delay such that the notification time is delayed relative to the time assigned to the use, and wherein the deliberate time delay is a shorter deliberate time delay when the event is an improper actuation event as opposed to a low inhalation event.

24. A method comprising:
determine a parameter relating to airflow during a use of an inhaler by a subject;
assign a time to the use;
determine inhalation information from the parameter relating to airflow; and
control a user interface to issue a notification at a notification time that the inhalation information is available, wherein the notification is issued at a deliberate time delay such that the notification time is delayed relative to the time assigned to the use, and wherein the time delay is a shorter deliberate time delay when the use of the inhaler by the subject is categorized as a no inhalation event or an excessive inhalation event as opposed to a low inhalation event or a good inhalation event.

25. The method of claim 24, wherein a time-and-date stamp is associated with the parameter, and wherein the deliberate time delay is configured such that the notification time is a predetermined time on a day which is subsequent to the day indicated by the time-and-date stamp.

26. The method of claim 24, wherein the no inhalation event is characterized by no inhalation being detected, or is characterized by an inhalation being detected but the parameter relating to the airflow being equal to or less than a first threshold;
wherein the excessive inhalation event is characterized by an inhalation being detected but the parameter relating to the airflow being higher than a second threshold; and
wherein the good inhalation event is characterized by an inhalation being detected, and the parameter relating to the airflow being equal to or less than the second predetermined threshold and greater than the first predetermined threshold.

* * * * *